United States Patent
Levi et al.

(10) Patent No.: US 11,328,400 B2
(45) Date of Patent: May 10, 2022

(54) METHOD AND SYSTEM FOR COMPUTER-AIDED ANEURYSM TRIAGE

(71) Applicant: Viz.ai Inc., San Francisco, CA (US)

(72) Inventors: Gil Levi, San Francisco, CA (US); Yoni Donner, San Francisco, CA (US); David Golan, San Francisco, CA (US); Christopher Mansi, San Francisco, CA (US)

(73) Assignee: Viz.ai Inc., San Francisco, CA (US)

( * ) Notice: Subject to any disclaimer, the term of this patent is extended or adjusted under 35 U.S.C. 154(b) by 0 days.

(21) Appl. No.: 17/385,326

(22) Filed: Jul. 26, 2021

(65) Prior Publication Data
US 2022/0028524 A1 Jan. 27, 2022

Related U.S. Application Data

(60) Provisional application No. 63/056,347, filed on Jul. 24, 2020.

(51) Int. Cl.
*G16H 50/20* (2018.01)
*G16H 30/20* (2018.01)
(Continued)

(52) U.S. Cl.
CPC ............. *G06T 7/00* (2013.01); *G06N 3/0454* (2013.01); *G06T 3/00* (2013.01); *G06T 3/0068* (2013.01);
(Continued)

(58) Field of Classification Search
None
See application file for complete search history.

(56) References Cited

U.S. PATENT DOCUMENTS

| 6,349,330 B1 | 2/2002 | Bernadett et al. |
| 8,374,414 B2 | 2/2013 | Tang et al. |

(Continued)

FOREIGN PATENT DOCUMENTS

| JP | 2004243117 A | 9/2004 |
| JP | 2012027565 A | 2/2012 |
| WO | 2016134125 A1 | 8/2016 |

OTHER PUBLICATIONS

Examination Report No. 1 for Australian Patent Application No. 2018288766 dated May 22, 2020.
(Continued)

*Primary Examiner* — Soo Shin
(74) *Attorney, Agent, or Firm* — Jeffrey Schox; Caitlin Ploch

(57) ABSTRACT

A system for computer-aided triage includes and/or interfaces with a computing system. A method for computer-aided triage includes receiving a data packet including a set of images; and processing the set of images to determine a suspected condition and/or associated features. Additionally or alternatively, the method can include any or all of: preprocessing the set of images; triggering an action based on the suspected condition and/or associated features; determining a recipient based on the suspected condition; preparing a data packet for transfer; transmitting information to a device associated with the recipient; receiving an input from the recipient and triggering an action based on the input; aggregating data; and/or any other suitable processes.

16 Claims, 13 Drawing Sheets

(51) Int. Cl.
  *G06T 7/10* (2017.01)
  *G06T 3/00* (2006.01)
  *G06N 3/04* (2006.01)
  *G06T 7/00* (2017.01)
(52) U.S. Cl.
  CPC ............... *G06T 7/10* (2017.01); *G16H 30/20* (2018.01); *G16H 50/20* (2018.01)

(56) References Cited

U.S. PATENT DOCUMENTS

| | | | |
|---|---|---|---|
| 9,307,918 | B2 | 4/2016 | Kin et al. |
| 10,346,979 | B2 | 7/2019 | Mansi et al. |
| 10,373,315 | B2 | 8/2019 | Mansi et al. |
| 10,853,449 | B1* | 12/2020 | Nguyen .................. G06N 3/084 |
| 2004/0161137 | A1 | 8/2004 | Aben et al. |
| 2006/0140473 | A1 | 6/2006 | Brooksby et al. |
| 2007/0019846 | A1* | 1/2007 | Bullitt .................... G06T 7/0014 382/128 |
| 2008/0021502 | A1 | 1/2008 | Imielinska et al. |
| 2009/0028403 | A1* | 1/2009 | Bar-Aviv ................ G16H 50/20 382/128 |
| 2009/0279752 | A1 | 11/2009 | Sirohey et al. |
| 2010/0106002 | A1 | 4/2010 | Sugiyama et al. |
| 2011/0052024 | A1 | 3/2011 | Nowinski |
| 2012/0065987 | A1 | 3/2012 | Farooq et al. |
| 2012/0201446 | A1 | 8/2012 | Yang et al. |
| 2012/0237103 | A1 | 9/2012 | Hu |
| 2013/0208966 | A1 | 8/2013 | Zhao et al. |
| 2014/0142982 | A1 | 5/2014 | Janssens |
| 2014/0142983 | A1 | 5/2014 | Backhaus et al. |
| 2014/0222444 | A1 | 8/2014 | Cerello et al. |
| 2014/0348408 | A1* | 11/2014 | Zhu ........................ A61B 6/032 382/132 |
| 2015/0104102 | A1 | 4/2015 | Carreira et al. |
| 2015/0320365 | A1 | 11/2015 | Schulze et al. |
| 2016/0037057 | A1 | 2/2016 | Westin et al. |
| 2016/0063191 | A1 | 3/2016 | Vesto et al. |
| 2016/0100302 | A1 | 4/2016 | Barash et al. |
| 2016/0110890 | A1 | 4/2016 | Smith |
| 2016/0135706 | A1 | 5/2016 | Sullivan et al. |
| 2016/0180042 | A1 | 6/2016 | Menon et al. |
| 2016/0188829 | A1 | 6/2016 | Southerland et al. |
| 2017/0007167 | A1 | 1/2017 | Kostic et al. |
| 2017/0143428 | A1 | 5/2017 | Raffy et al. |
| 2017/0147765 | A1 | 5/2017 | Mehta |
| 2017/0228516 | A1 | 8/2017 | Sampath et al. |
| 2017/0258433 | A1 | 9/2017 | Gulsun et al. |
| 2017/0300654 | A1 | 10/2017 | Stein et al. |
| 2017/0340260 | A1 | 11/2017 | Chowdhury et al. |
| 2018/0025255 | A1 | 1/2018 | Poole et al. |
| 2018/0085001 | A1 | 3/2018 | Berger et al. |
| 2018/0110475 | A1 | 4/2018 | Shaya |
| 2018/0116620 | A1 | 5/2018 | Chen et al. |
| 2018/0253530 | A1 | 9/2018 | Goldberg et al. |
| 2018/0365824 | A1* | 12/2018 | Yuh ........................ G06T 7/0012 |
| 2018/0366225 | A1 | 12/2018 | Mansi et al. |
| 2019/0380643 | A1 | 12/2019 | Kochura et al. |
| 2020/0058410 | A1 | 2/2020 | Khouri et al. |
| 2020/0090331 | A1 | 3/2020 | Mansi et al. |
| 2020/0294241 | A1* | 9/2020 | Wu .......................... G06T 7/10 |
| 2021/0137384 | A1* | 5/2021 | Robinson ............. A61B 5/0036 |
| 2021/0334958 | A1* | 10/2021 | Siow ..................... G06T 7/0012 |

OTHER PUBLICATIONS

Extended EP Search Report for EP Application No. 18821318.5 dated Dec. 23, 2020.
International Search Report and Written Opinion for International Application No. PCT/US2018/038334 dated Aug. 30, 2018.
International Search Report and Written Opinion for PCT Application No. PCT/US20/39903 dated Sep. 4, 2020.
Cai, Zhaowei, et al., "Cascade R-CNN: High Quality Object Detection and Instance Segmentation", https://arxiv.org/pdf/1906.09756.pdf, Jun. 24, 2019.
He, Kaiming, et al., "Mask R-CNN", https://arxiv.org/pdf/1703.06870.pdf, Jan. 24, 2018.
Ker, Justin, et al., "Image Thresholding Improves 3-Dimensional Convolutional Neural Network 1-21 Diagnosis of Different Acute Brain Hemorrhages on Computed Tomography Scans", Sensors 2019, 2167,May 10, 2019, www.mdpi.com.com/journal/sensors.
Keshavamurthy, K., et al., "Machine learning algorithm for automatic detection of CT-identifiable hyperdense lesions associated with traumatic brain injury", Mar. 23, 2017, SPIE Medical Imaging, Orlando, Florida.
Kirisil, H.A., et al., "Standardized evaluation framework for evaluating coronary artery stenosis detection, stenosis quantification and lumen segmentation algorithms in computed tomography angiography", Elsevier, 2013, pp. 859-876.
Lewis, Thomas L., et al., "Ambulance smartphone tool for field triage of ruptured aortic aneurysms (FILTR): study protocol for a prospective observational validation of diagnostic accuracy", BMJ Open 2016, pp. 1-5 , https://bmjopen.bmj.com/content/bmjopen/6/10/e011308.full.pdf.
Lidayova, Kristina, et al., "Skeleton-based 1-3,6-15 fast, fully automated generation of vessel tree structure for clinical evaluation of blood vessel systems", In: Skeletonization : theory, methods and applications, Jun. 1, 2017.
Liu, Liyuan, et al., "On the Variance of the Adaptive Learning Rate and Beyond", https://arxiv.org/pdf/1908.03265.pdf, Apr. 17, 2020, Published as a conference paper at ICLR 2020.
Madhuripan, Nikhil, et al., "Computed Tomography Angiography in Head and Neck Emergencies", Seminars in Ultrasound and CT and MRI, US, vol. 38, No. 4, 2017. Feb. 20, 2017 (Feb. 20, 2017), pp. 345-356.
Smith, Wade S., et al., "Prognostic Significance of Angiographically Confirmed Large Vessel Intracranial Occlusion in Patients Presenting With Acute Brain Ischemia", Neurocritical Care, vol. 4, 2006.
Yu, Y. , et al., "Use of Deep Learning to Predict Final Ischemic Stroke Lesions From Initial Magnetic Resonance Imaging", Mar. 1, 2020, https://europepmc.org/article/med/32163165.

* cited by examiner

ABSTRACT

METHOD AND SYSTEM FOR COMPUTER-AIDED ANEURYSM TRIAGE

CROSS-REFERENCE TO RELATED APPLICATIONS

This application claims the benefit of U.S. Provisional Application No. 63/056,347, filed 24 Jul. 2020, which is incorporated in its entirety by this reference.

TECHNICAL FIELD

This invention relates generally to the medical triage field, and more specifically to a new and useful system and method for computer-aided aneurysm triage in the medical triage field.

BACKGROUND

In current triaging workflows, especially those in an emergency setting, a patient presents at a first point of care, where imaging is performed. The image data is then sent to a standard radiology workflow, which typically involves: images (equivalently referred to herein as instances) being uploaded to a radiologist's queue, the radiologist reviewing the images at a workstation, the radiologist generating a report, an emergency department doctor reviewing the radiologist's report, the emergency department doctor determining a specialist to contact, and making a decision of how to treat and/or transfer the patient (e.g., to a $2^{nd}$ point of care). This workflow is typically very time-consuming, which increases the time it takes to treat and/or transfer a patient to a specialist.

This can be especially complicated in instances involving patients presenting with an aneurysm, as not only are aneurysms often difficult to spot (e.g., due to their small size), but the next steps for treatment are often ambiguous and subjective. In some cases, for instance, an aneurysm might be left untreated with no explicit plans for follow-up imaging made, which could potentially cause dangerous and sometimes fatal consequences. In other cases, the aneurysm might not be detected at all in the conventional workflow (e.g., due to its small size).

Thus, there is a need in the medical triage field to create an improved and useful system and method for decreasing the time it takes to identify and initiate treatment for a patient presenting with a critical condition such as an aneurysm.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
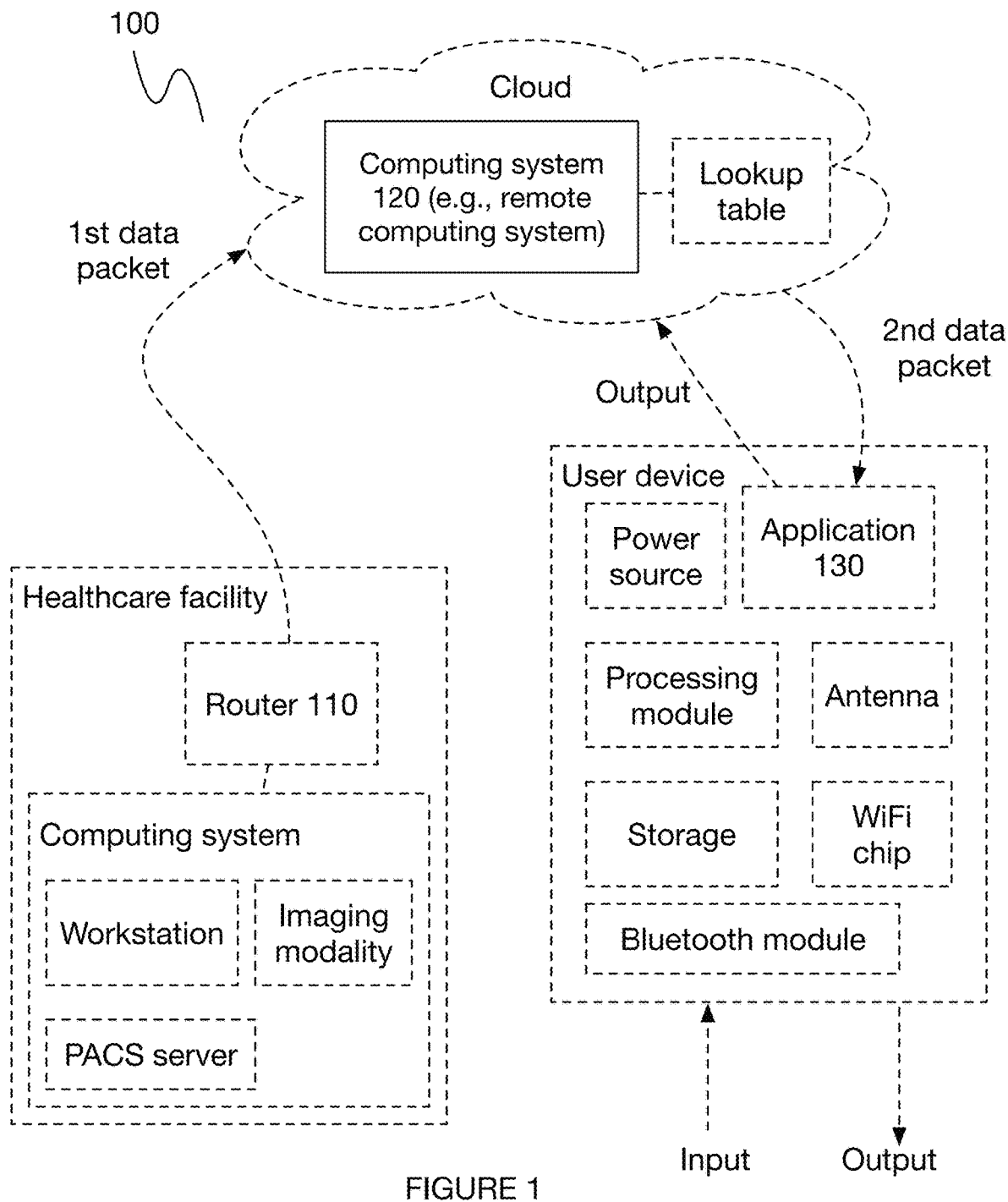
FIG. 1 is a schematic of a system for computer-aided triage.

As shown in FIG. 1, a system 100 for computer-aided triage includes and/or interfaces with a computing system. Additionally or alternatively, the system 100 can include and/or interface with any or all of: a router, a client application, any number of computing systems (e.g., local, remote), servers (e.g., PACS server), storage, lookup table, memory, and/or any other suitable components or combination of components. Further additionally or alternatively, the system can include any or all of the components, embodiments, and examples as described in any or all of: U.S. application Ser. No. 16/012,458, filed 19 Jun. 2018; U.S. application Ser. No. 16/012,495, filed 19 Jun. 2018; U.S. application Ser. No. 16/688,721, filed 19 Nov. 2019; U.S. application Ser. No. 16/913,754, filed 26 Jun. 2020; U.S. application Ser. No. 16/938,598, filed 24 Jul. 2020; and U.S. application Ser. No. 17/001,218, filed 24 Aug. 2020; each of which is incorporated herein in its entirety by this reference.

Figure 2:
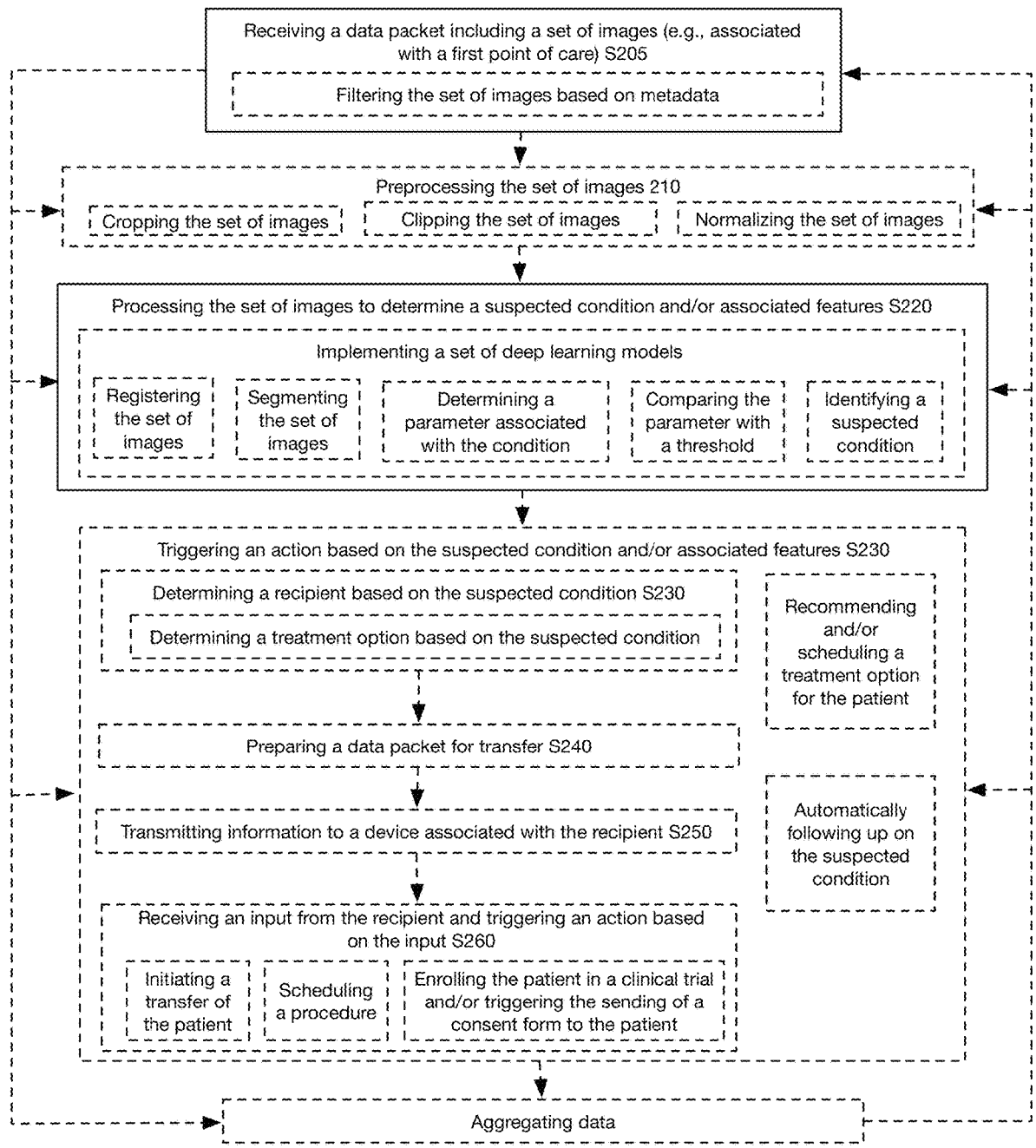
FIG. 2 is a schematic of a method for computer-aided triage.
Figure 3:
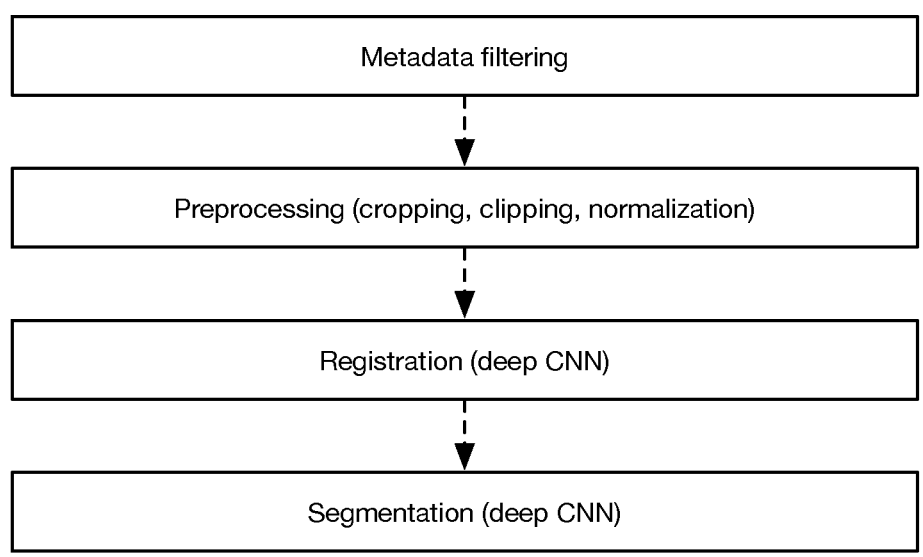
FIG. 3 is a schematic of an algorithm for computer-aided aneurysm detection.

As shown in FIG. 2, the method 200 includes receiving a data packet including a set of images S205; and processing the set of images to determine a suspected condition and/or associated features S220. Additionally or alternatively, the method 200 can include any or all of: preprocessing the set of images S210; triggering an action based on the suspected condition and/or associated features S230; determining a recipient based on the suspected condition S232; preparing a data packet for transfer S234; transmitting information to a device associated with the recipient S236; receiving an input from the recipient and triggering an action based on the input S238; aggregating data; and/or any other suitable processes.

Further additionally or alternatively, the method 200 can include any or all of the processes, embodiments, and examples described in any or all of: U.S. application Ser. No. 16/012,458, filed 19 Jun. 2018; U.S. application Ser. No. 16/012,495, filed 19 Jun. 2018; U.S. application Ser. No. 16/688,721, filed 19 Nov. 2019; U.S. application Ser. No. 16/913,754, filed 26 Jun. 2020; U.S. application Ser. No. 16/938,598, filed 24 Jul. 2020; and U.S. application Ser. No. 17/001,218, filed 24 Aug. 2020; each of which is incorporated herein in its entirety by this reference, and/or any other suitable processes performed in any suitable order. The method 200 can be performed with a system as described above and/or any other suitable system.

2. Benefits

The system and method for computer-aided aneurysm triage can confer several benefits over current systems and methods.

In a first set of variations, the system and/or method confer the benefit of reducing the time to match and/or transfer a patient presenting with a condition (e.g., aneurysm) to a specialist. In a specific example, for instance, the average time between generating a scan and notifying a specialist (e.g., in a case associated with a suspected condition) is reduced from over 30 minutes (e.g., 35 minutes, 40 minutes, 45 minutes, 50 minutes, greater than 50 minutes, etc.) to less than 8 minutes (e.g., 30 seconds, less than a minute, between 1-2 minutes, 2 minutes, between 2-3 minutes, 3 minutes, between 3-4 minutes, etc.). This can additionally or alternatively function to reduce the time it takes to match the patient with a clinical trial (e.g., to notify a principal investigator associated with the clinical trial).

In these variations and others, numerous further benefits can be conferred, such as a reduced time to treatment, a reduced time to transferring to a $2^{nd}$ point of care (e.g., stroke center), a reduced time to clinical trial approval and enrollment, an improved patient outcome (e.g., upon detecting a small aneurysm, upon enabling the monitoring of a detected aneurysm, based on enabled communication/collaboration between members of the patient care team, etc.), and/or any other outcomes.

In a second set of variations, additional or alternative to the first, the system and/or method confer the benefit of enabling aneurysms, including small aneurysms (e.g., less than 5 mm, less than 4 mm, less than 3 mm, less than 2 mm, less than 1 mm, greater than 2 mm, etc.), to be reliably detected. In specific examples, the method described below enables aneurysms to be detected more reliably than by a radiologist (e.g., a junior radiologist, radiologist who might find a first aneurysm and stop looking for others, etc.). The system and/or method can additionally or alternatively enable consistent treatment options to be triggered for patients found to have an aneurysm. In some examples, for instance, a treatment option and/or associated specialist can be triggered based on the size and/or location of the detected aneurysm (e.g., aneurysms larger than 5 mm are treated, aneurysms larger than 3 mm and on the basilar artery are treated, aneurysms less than a predetermined threshold are recommended for a follow up to monitor, etc.).

In a third set of variations, additional or alternative to those described above, the system and/or method provide a parallel process to a traditional workflow (e.g., standard radiology workflow), which can confer the benefit of reducing the time to determine a treatment option while having the outcome of the traditional workflow as a backup in the case that an inconclusive or inaccurate determination (e.g., false negative, false positive, etc.) results from the method. Additionally or alternatively, the system and/or method can be implemented in place of and/or integrated within a traditional workflow (e.g., the standard radiology workflow) and/or otherwise integrated with or independent from any suitable workflows.

In a fourth set of variations, additional or alternative to those described above, the system and/or method confer the benefit of minimizing the occurrence of false positive cases (e.g., less than 10% occurrence, less than 5% occurrence, which functions to minimize disturbances caused to specialists or other individuals. This can function to minimize unnecessary disturbances to specialists in variations in which specialists or other users are notified on a mobile device upon detection of a potential aneurysm, as it can minimize the occurrence of a specialist being alerted (e.g., potentially at inconvenient times of day, while the specialist is otherwise occupied, etc.) for false positives, while still maintaining a fallback in the standard radiology workflow in the event that a true positive is missed. In a set of specific examples, the method includes training (e.g., iteratively training) a set of deep learning models involved in aneurysm detection on images originally detected to be a true positive but later identified as a false positive.

In a fifth set of variations, additional or alternative to those described above, the system and/or method confer the benefit of reorganizing a queue of patients, wherein patients having a certain condition are detected early and prioritized (e.g., moved to the front of the queue).

In a sixth set of variations, additional or alternative to those described above, the system and/or method confer the benefit of determining actionable analytics to optimize a workflow, such as a triage workflow.

In a seventh set of variations, additional or alternative to those described above, the system and/or method confer the benefit of recommending a patient for a clinical trial based on an automated processing of a set of images (e.g., brain images) associated with the patient.

In an eighth set of variations, additional or alternative to those described above, the system and/or method confer the benefit of determining a suspected patient condition with a sensitivity of at least 95% (e.g., 96%, 97%, between 96% and 97%, etc.) and a specificity of at least 94% (e.g., 96%, 97%, between 96% and 97%, etc.).

In a ninth set of variations, additional or alternative to those described above, the system and/or method confer the benefit of enabling small aneurysms (e.g., diameter less than 5 mm, less than 4 mm, less than 3 mm, less than 2 mm, less than 1 mm, etc.) to be reliably detected based on CT images rather than MRI images.

Additionally or alternatively, the system and method can confer any other benefits.

3. System

The system preferably interfaces with one or more points of care (e.g., $1^{st}$ point of care, $2^{nd}$ point of care, $3^{rd}$ point of care, etc.), each of which are typically a healthcare facility. A $1^{st}$ point of care herein refers to the healthcare facility at which a patient presents, typically where the patient first presents (e.g., in an emergency setting). Conventionally, healthcare facilities include spoke facilities, which are often general (e.g., non-specialist, emergency, etc.) facilities, and hub (e.g., specialist) facilities, which can be equipped or better equipped (e.g., in comparison to spoke facilities) for certain procedures (e.g., mechanical thrombectomy), conditions (e.g., stroke), or patients (e.g., high risk). Patients typically present to a spoke facility at a $1^{st}$ point of care, but can alternatively present to a hub facility, such as when it is evident what condition their symptoms reflect, when they have a prior history of a serious condition, when the condition has progressed to a high severity, when a hub facility is closest, randomly, or for any other reason. A healthcare facility can include any or all of: a hospital, clinic, ambulances, doctor's office, imaging center, laboratory, primary stroke center (PSC), comprehensive stroke center (CSC), stroke ready center, interventional ready center, or any other suitable facility involved in patient care and/or diagnostic testing.

A patient can be presenting with symptoms of a condition, no symptoms (e.g., presenting for routine testing), or for any other suitable system. In some variations, the patient is presenting with one or more symptoms consistent with an aneurysm (e.g., visual disturbances such as loss of vision and/or double vision, pain above and/or around eye, numbness or weakness on side of face, difficulty speaking, headache, loss of balance, difficulty concentrating, problems with short-term memory, etc.) and/or stroke (e.g., weakness, numbness, speech abnormalities, and facial drooping). Typically, these patients are then sent for an imaging protocol at an imaging modality, such as, but not limited to: a non-contrast CT (NCCT) scan of the head, a CTA scan of the head and neck, a CT perfusion (CTP) scan of the head.

A healthcare worker herein refers to any individual or entity associated with a healthcare facility, such as, but not limited to: a physician, emergency room physician (e.g., orders appropriate lab and imaging tests in accordance with a stroke protocol), radiologist (e.g., on-duty radiologist, healthcare worker reviewing a completed imaging study, healthcare working authoring a final report, etc.), neuroradiologist, specialist (e.g., neurovascular specialist, vascular neurologist, neuro-interventional specialist, neuro-endovascular specialist, expert/specialist in a procedure such as mechanical thrombectomy, cardiac specialist, etc.), administrative assistant, healthcare facility employee (e.g., staff employee), emergency responder (e.g., emergency medical technician), or any other suitable individual.

The image data can include computed tomography (CT) data (e.g., radiographic CT, non-contrast CT, CT perfusion, etc.), preferably non-contrast CT data (e.g., axial data, axial series of slices, consecutive slices, etc.) but can additionally or alternatively any other suitable image data. The image data is preferably generated at an imaging modality (e.g., scanner at the $1^{st}$ point of care), such as a CT scanner, magnetic resonance imaging (MRI) scanner, ultrasound system, or any other scanner. Additionally or alternatively, image data can be generated from a camera, user device, accessed from a database or web-based platform, drawn, sketched, or otherwise obtained.

3.1 System—Router 110

The system 100 can include a router 110 (e.g., medical routing system), which functions to receive a data packet (e.g., dataset) including instances (e.g., images, scans, etc.) taken at an imaging modality (e.g., scanner) via a computing system (e.g., scanner, workstation, PACS server) associated with a $1^{st}$ point of care. The instances are preferably in the Digital Imaging and Communications in Medicine (DICOM) file format, as well as generated and transferred between computing system in accordance with a DICOM protocol, but can additionally or alternatively be in any suitable format. Additionally or alternatively, the instances can include any suitable medical data (e.g., diagnostic data, patient data, patient history, patient demographic information, etc.), such as, but not limited to, PACS data, Health-Level 7 (HL7) data, electronic health record (EHR) data, or any other suitable data, and to forward the data to a remote computing system.

The instances preferably include (e.g., are tagged with) and/or associated with a set of metadata, but can additionally or alternatively include multiple sets of metadata, no metadata, extracted (e.g., removed) metadata (e.g., for regulatory purposes, HIPAA compliance, etc.), altered (e.g., encrypted, decrypted, deidentified, anonymized etc.) metadata, or any other suitable metadata, tags, identifiers, or other suitable information.

The router 110 can refer to or include a virtual entity (e.g., virtual machine, virtual server, etc.) and/or a physical entity (e.g., local server). The router can be local (e.g., at a $1^{st}$ healthcare facility, $2^{nd}$ healthcare facility, etc.) and associated with (e.g., connected to) any or all of: on-site server associated with any or all of the imaging modality, the healthcare facility's PACS architecture (e.g., server associated with physician workstations), or any other suitable local server or DICOM compatible device(s). Additionally or alternatively, the router can be remote (e.g., locate at a remote facility, remote server, cloud computing system, etc.), and associated with any or all of: a remote server associated with the PACS system, a modality, or another DICOM compatible device such as a DICOM router.

The router 110 preferably operates on (e.g., is integrated into) a system (e.g., computing system, workstation, server, PACS server, imaging modality, scanner, etc.) at a $1^{st}$ point of care but additionally or alternatively, at a $2^{nd}$ point of care, remote server (e.g., physical, virtual, etc.) associated with one or both of the $1^{st}$ point of care and the $2^{nd}$ point of care (e.g., PACS server, EHR server, HL7 server), a data storage system (e.g., patient records), or any other suitable system. In some variations, the system that the router operates on is physical (e.g., physical workstation, imaging modality, scanner, etc.) but can additionally or alternatively include virtual components (e.g., virtual server, virtual database, cloud computing system, etc.).

The router 110 is preferably configured to receive data (e.g., instances, images, study, series, etc.) from an imaging modality, preferably an imaging modality (e.g., CT scanner, MRI scanner, ultrasound machine, etc.) at a first point of care (e.g., spoke, hub, etc.) but can additionally or alternatively be at a second point of care (e.g., hub, spoke, etc.), multiple points of care, or any other healthcare facility. The router can be coupled in any suitable way (e.g., wired connection, wireless connection, etc.) to the imaging modality (e.g., directly connected, indirectly connected via a PACS server, etc.). Additionally or alternatively, the router can be connected to the healthcare facility's PACS architecture, or other server or DICOM-compatible device of any point of care or healthcare facility.

In some variations, the router includes a virtual machine operating on a computing system (e.g., computer, workstation, user device, etc.), imaging modality (e.g., scanner), server (e.g., PACS server, server at $1^{st}$ healthcare facility, server at $2^{nd}$ healthcare facility, etc.), or other system. In a specific example, the router is part of a virtual machine server. In another specific example, the router is part of a local server.

3.2 System—Remote Computing System 120

The system 100 can include a remote computing system 120, which can function to receive and process data packets (e.g., dataset from router), determine a treatment option (e.g., select a $2^{nd}$ point of care, select a specialist, etc.), interface with a user device (e.g., mobile device), compress a data packet, extract and/or remove metadata from a data packet (e.g., to comply with a regulatory agency), or perform any other suitable function.

Preferably, part of the method 200 is performed at the remote computing system (e.g., cloud-based), but additionally or alternatively all of the method 200 can be performed at the remote computing system, the method 200 can be performed at any other suitable computing system(s). In some variations, the remote computing system 120 provides an interface for technical support (e.g., for a client application) and/or analytics. In some variations, the remote computing system includes storage and is configured to store and/or access a lookup table, wherein the lookup table functions to determine a treatment option (e.g., $2^{nd}$ point of care), a contact associated with the $2^{nd}$ point of care, and/or any other suitable information.

In some variations, the remote computing system 120 connects multiple healthcare facilities (e.g., through a client application, through a messaging platform, etc.).

In some variations, the remote computing system 120 functions to receive one or more inputs and/or to monitor a set of client applications (e.g., executing on user devices, executing on workstations, etc.).

3.3 System—Application 130

Figure 5A:
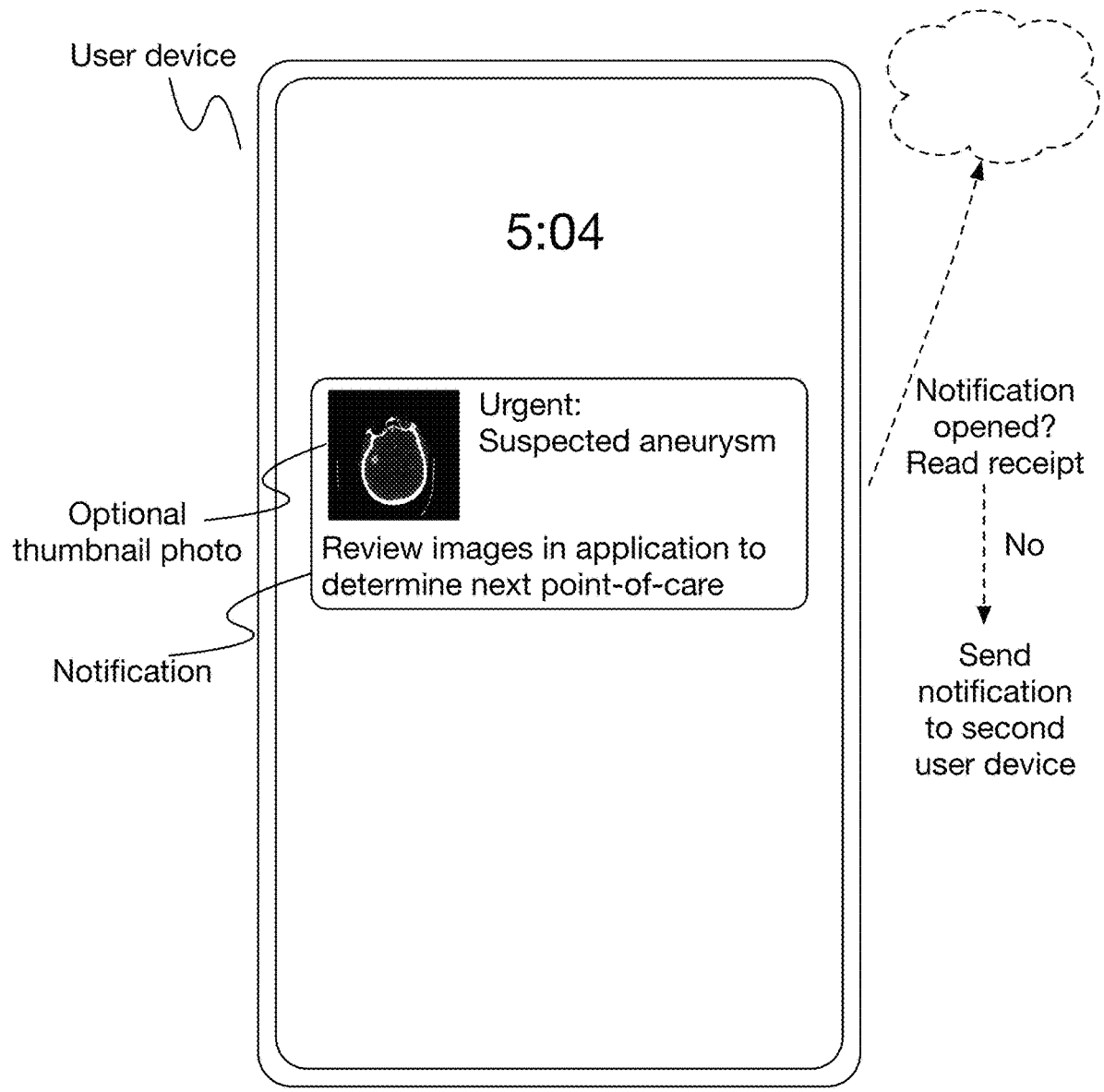
FIGS. 5A-5B depict a variation of an application on a user device.
Figure 5B:
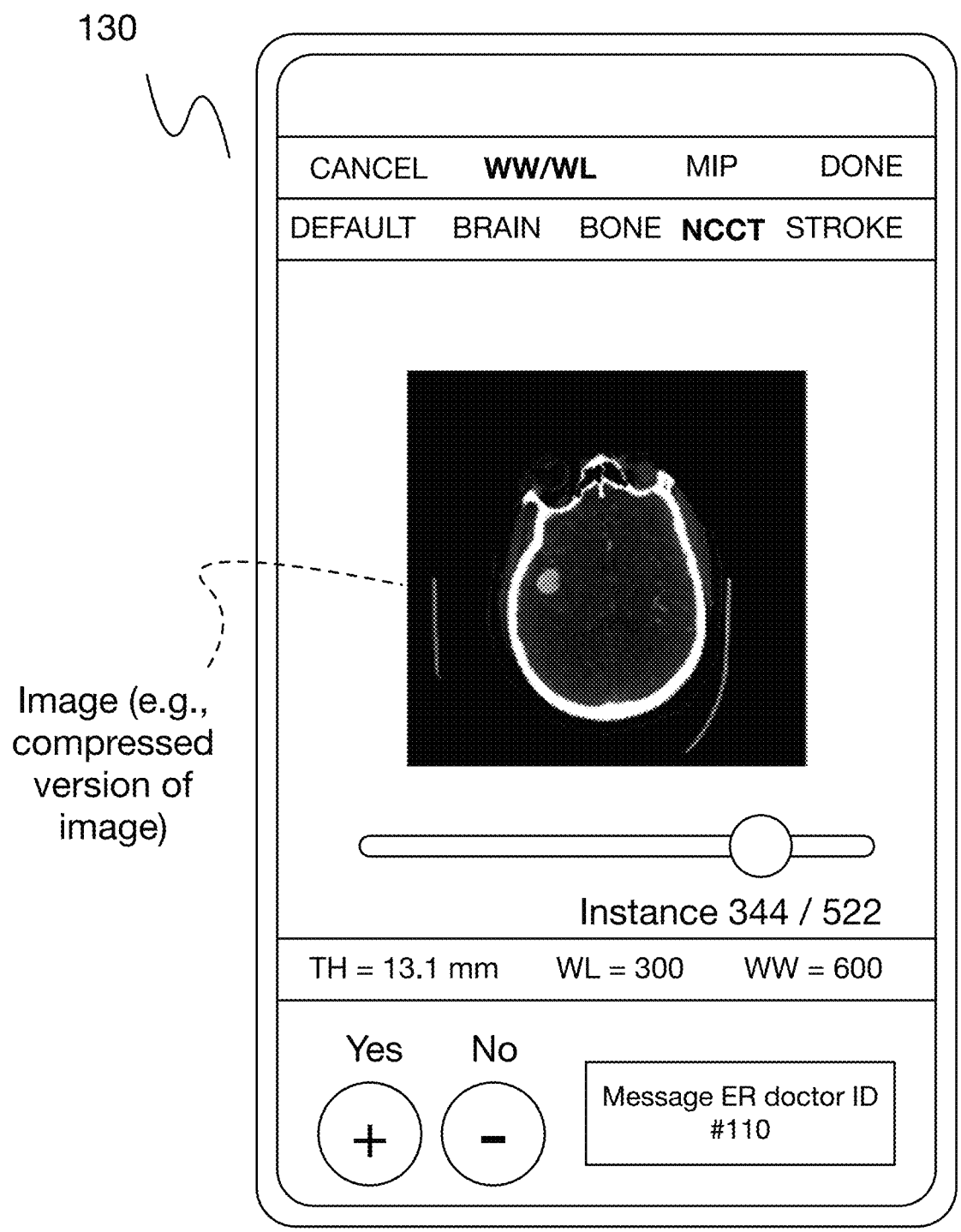

The system 100 can include one or more applications 130 (e.g., clients, client applications, client application executing on a device, etc.), such as the application shown in FIGS. 5A and 5B, which individually or collectively function to provide one or more outputs (e.g., from the remote computing system) to a contact. Additionally or alternatively, the applications can individually or collectively function to receive one or more inputs from a contact, provide one or more outputs to a healthcare facility (e.g., first point of care, second point of care, etc.), establish communication between healthcare facilities, or perform any other suitable function.

In some variations, one or more features of the application (e.g., appearance, information content, information displayed, user interface, graphical user interface, etc.) are determined based on any or all of: the type of device that the application is operating on (e.g., user device vs. healthcare facility device, mobile device vs. stationary device), where the device is located (e.g., $1^{st}$ point of care, $2^{nd}$ point of care, etc.), who is interacting with the application (e.g., user identifier, user security clearance, user permission, etc.), or any other characteristic. In some variations, for instance, an application executing on a healthcare facility will display a $1^{st}$ set of information (e.g., uncompressed images, metadata, etc.) while an application executing on a user device will display a $2^{nd}$ set of information (e.g., compressed images, no metadata, etc.). In some variations, the type of data to display is determined based on any or all of: an application identifier, mobile device identifier, workstation identifier, or any other suitable identifier.

The outputs of the application can include any or all of: an alert or notification (e.g., push notification, text message, call, email, etc.); an image set (e.g., compressed version of images taken at scanner, preview of images taken at scanner, images taken at scanner, etc.); a set of tools for interacting with the image set, such as any or all of panning, zooming, rotating, adjusting window level and width, scrolling, performing maximum intensity projection [MIP] (e.g., option to select the slab thickness of a MIP), changing the orientation of a 3D scan (e.g., changing between axial, coronal, and sagittal views, freestyle orientation change), showing multiple views of a set of images; a worklist (e.g., list of patients presenting for and/or requiring care, patients being taken care of by specialist, patients recommended to specialist, procedures to be performed by specialist, etc.); a messaging platform (e.g., HIPAA-compliant messaging platform, texting platform, video messaging, group messaging etc.); a telecommunication platform (e.g., video conferencing platform); a directory of contact information (e.g., $1^{st}$ point of care contact info, $2^{nd}$ point of care contact info, etc.); tracking of a workflow or activity (e.g., real-time or near real-time updates of patient status/workflow/etc.); analytics based on or related to the tracking (e.g., predictive analytics such as predicted time remaining in radiology workflow or predicted time until stroke reaches a certain severity; average time in a workflow; average time to transition to a second point of care, etc.); or any other suitable output.

The inputs can include any or all of the outputs described previously, touch inputs (e.g., received at a touch-sensitive surface), audio inputs, optical inputs, or any other suitable input. The set of inputs preferably includes an input indicating receipt of an output by a recipient (e.g., read receipt of a specialist upon opening a notification). This can include an active input from the contact (e.g., contact makes selection at application), a passive input (e.g., read receipt), or any other input.

In one variation, the system 100 includes a mobile device application 130 and a workstation application 130—both connected to the remote computing system—wherein a shared user identifier (e.g., specialist account, user account, etc.) can be used to connect the applications (e.g., retrieve a case, image set, etc.) and determine the information to be displayed at each application (e.g., variations of image datasets). In one example, the information to be displayed (e.g., compressed images, high-resolution images, etc.) can be determined based on: the system type (e.g., mobile device, workstation), the application type (e.g., mobile device application, workstation application), the user account (e.g., permissions, etc.), any other suitable information, or otherwise determined.

The application can include any suitable algorithms or processes for analysis, and part or all of the method 200 can be performed by a processor associated with the application.

The application preferably includes both front-end (e.g., application executing on a user device, application executing on a workstation, etc.) and back-end components (e.g., software, processing at a remote computing system, etc.), but can additionally or alternatively include just front-end or back-end components, or any number of components implemented at any suitable system(s).

3.4 System—Additional Components

The system 100 and/or or any component of the system 100 can optionally include or be coupled to any suitable component for operation, such as, but not limited to: a processing module (e.g., processor, microprocessor, etc.), control module (e.g., controller, microcontroller), power module (e.g., power source, battery, rechargeable battery, mains power, inductive charger, etc.), sensor system (e.g., optical sensor, camera, microphone, motion sensor, location sensor, etc.), or any other suitable component.

4. Method

As shown in FIG. 2, the method 200 includes receiving a data packet including a set of images S205; and processing the set of images to determine a suspected condition and/or associated features S220. Additionally or alternatively, the method 200 can include any or all of: preprocessing the set of images S210; triggering an action based on the suspected condition and/or associated features S230; determining a recipient based on the suspected condition S232; preparing a data packet for transfer S234; transmitting information to a device associated with the recipient S236; receiving an input from the recipient and triggering an action based on the input S238; aggregating data; and/or any other suitable processes.

Further additionally or alternatively, the method 200 can include any or all of the processes, embodiments, and examples described in any or all of: U.S. application Ser. No. 16/012,458, filed 19 Jun. 2018; U.S. application Ser. No. 16/012,495, filed 19 Jun. 2018; U.S. application Ser. No. 16/688,721, filed 19 Nov. 2019; U.S. application Ser. No.

16/913,754, filed 26 Jun. 2020; U.S. application Ser. No. 16/938,598, filed 24 Jul. 2020; and U.S. application Ser. No. 17/001,218, filed 24 Aug. 2020; each of which is incorporated herein in its entirety by this reference, and/or any other suitable processes performed in any suitable order. The method 200 can be performed with a system as described above and/or any other suitable system.

Figure 4:
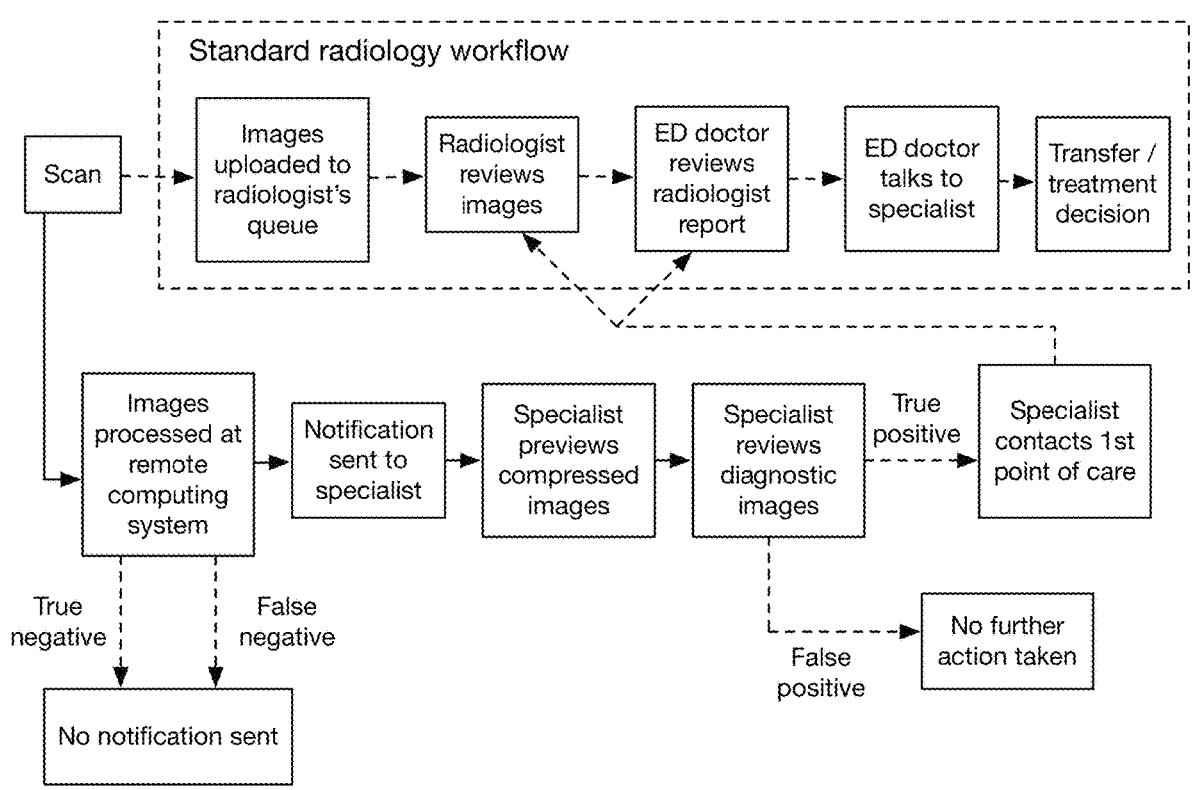
FIG. 4 depicts a variation of a method for computer-aided triage.

The method 200 is preferably performed separate from but in parallel with (e.g., contemporaneously with, concurrently with, etc.) a standard radiology workflow (e.g., as shown in FIG. 4), but can additionally or alternatively be implemented within a standard workflow, be performed at a separate time with respect to a standard workflow, or be performed at any suitable time.

The method 200 can be partially or fully implemented with the system 100 or with any other suitable system.

The method 200 functions to improve communication across healthcare workers (e.g., specialists, members of a care team, etc.) and/or healthcare facility networks (e.g., stroke networks, spokes and hubs, etc.) and increase the ability to detect (and optionally decrease the time required to detect and/or transfer a patient) having a suspected condition (e.g., brain condition, aneurysm, un-ruptured aneurysm, stroke, hemorrhagic stroke, hemorrhage, intracerebral hemorrhage (ICH), ischemic stroke, large vessel occlusion (LVO), cardiac event, trauma, etc.). In some variations, the method functions to enable the transfer (and optionally decrease the time to transfer) a patient from a first point of care (e.g., spoke, non-specialist facility, stroke center, ambulance, etc.) to a second point of care (e.g., hub, specialist facility, comprehensive stroke center, etc.), wherein the second point of care refers to a healthcare facility equipped to treat the patient. In some variations, the second point of care is the first point of care, wherein the patient is treated at the healthcare facility to which he or she initially presents.

The method 200 can optionally function as a parallel workflow tool, wherein the parallel workflow is performed contemporaneously with (e.g., concurrently, during, partially during) a standard radiology workflow (e.g., radiologist queue), but can additionally or alternatively be implemented within a standard workflow (e.g., to automate part of a standard workflow process, decrease the time required to perform a standard workflow process, etc.), be performed during a workflow other than a radiology workflow (e.g., during a routine examination workflow), or at any other suitable time.

The method 200 is preferably performed in response to a patient presenting at a first point of care. The first point of care can be an emergency setting (e.g., emergency room, ambulance, imaging center, etc.), equivalently referred to herein as an acute setting, or any suitable healthcare facility, such as those described previously. The patient is typically presenting with (or suspected to be presenting with), a neurovascular condition (e.g., aneurysm, un-ruptured aneurysm, stroke, etc.), cardiac event or condition (e.g., cardiovascular condition, heart attack, etc.), trauma (e.g., acute trauma, blood loss, etc.), or any other condition (e.g., life-threatening condition, time-sensitive condition, non-time-sensitive condition, etc.). In other variations, the method is performed for a patient presenting to a routine healthcare setting (e.g., non-emergency setting, clinic, imaging center, etc.), such as for routine testing, screening, diagnostics, imaging, clinic review, laboratory testing (e.g., blood tests), or for any other reason.

Any or all of the method can be performed using any number of machine learning (e.g., deep learning) or computer vision modules. Each module can utilize one or more of: supervised learning (e.g., using logistic regression, using back propagation neural networks, using random forests, decision trees, etc.), unsupervised learning (e.g., using an Apriori algorithm, using K-means clustering), semi-supervised learning, reinforcement learning (e.g., using a Q-learning algorithm, using temporal difference learning), and any other suitable learning style. Each module of the plurality can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, $C_{4-5}$, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial least squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and any suitable form of machine learning algorithm. Each module can additionally or alternatively be a: probabilistic module, heuristic module, deterministic module, or be any other suitable module leveraging any other suitable computation method, machine learning method, or combination thereof.

Each module can be validated, verified, reinforced, calibrated, or otherwise updated based on newly received, up-to-date measurements; past measurements recorded during the operating session; historic measurements recorded during past operating sessions; or be updated based on any other suitable data. Each module can be run or updated: once; at a predetermined frequency; every time the method is performed; every time an unanticipated measurement value is received; or at any other suitable frequency. The set of modules can be run or updated concurrently with one or more other modules, serially, at varying frequencies, or at any other suitable time. Each module can be validated, verified, reinforced, calibrated, or otherwise updated based on newly received, up-to-date data; past data or be updated based on any other suitable data. Each module can be run or updated: in response to determination of an actual result differing from an expected result; or at any other suitable frequency.

Additionally or alternatively, the method 200 can function to recruit patients for clinical trials (e.g., automatically based on processing a set of images and comparing with a set of clinical trial inclusion criteria), establish communication between a clinical trial research coordinator and a specialist, approve a patient for a clinical trial (e.g., by consensus of multiple individuals in communication through the client application), send a consent form to a patient, and/or perform any other suitable functions.

4.1 Method—Receiving a Data Packet Including a Set of Images Associated with a First Point of Care S205

The method 200 includes receiving a data packet associated with a patient and taken at a first point of care S205, which functions to collect data relevant to assessing a patient condition. Additionally or alternatively, S205 can function to initiate the method 200 (e.g., to trigger any or all of the subsequent processes of the method 200) and/or can perform any other functions.

S205 is preferably performed initially in the method 200, but can additionally or alternatively be performed in parallel with any other processes of the method 200, in response to any other processes of the method 200, multiple times, and/or at any other times. Additionally or alternatively, S205 can be performed at any other times and/or the method 200 can be performed in absence of S205.

The data is preferably received at a router 110, wherein the router is in the form of a virtual machine operating on a computing system (e.g., computer, workstation, quality assurance (QA) workstation, reading workstation, PACS server, etc.) coupled to or part of an imaging modality (e.g., CT scanner, MRI scanner, etc.), or any other suitable router. Additionally or alternatively, data can be received at a remote computing system (e.g., from an imaging modality, from a database, a server such as a PACS server, an internet search, social media, etc.), or at any other suitable computing system (e.g., server) or storage site (e.g., database). In some variations, for instance, a subset of the data (e.g., image data) is received at the router while another subset of the data (e.g., patient information, patient history, etc.) is received at a remote computing system. In a specific example, the data subset received at the router is eventually transmitted to the remote computing system for analysis.

S205 is preferably performed in response to (e.g., after, in real time with, substantially in real time with, with a predetermined delay, with a delay of less than 10 seconds, with a delay of less than 1 minute, at the prompting of a medical professional, etc.) the data (e.g., each of a set of instances) being generated at the imaging modality. Additionally or alternatively, S205 can be performed in response to a set of multiple instances being generated by the imaging modality (e.g., after a partial series has been generated, after a full series has been generated, after a study has been generated, etc.), in response to a metadata tag being generated (e.g., for an instance, for a series, for a study, etc.), in response to a trigger (e.g., request for images), throughout the method (e.g., as a patient's medical records are accessed, as information is entered a server, as information is retrieved from a server, etc.), or at any other suitable time.

S205 can be performed a single time or multiple times (e.g., sequentially, at different times in the method, once patient condition has progressed, etc.). In one variation, each instance is received (e.g., at a router, at a remote computing system, etc.) individually as it is generated. In a second variation, a set of multiple instances (e.g., multiple images, full series, etc.) are received together (e.g., after a scan has completed, after a particular anatomical component has been imaged, etc.).

The set of images are preferably in the form of computed tomography angiograms (CTAs), from a CT scanner, but can additionally or alternatively include any other suitable images, such as—but not limited to—any or all of: any suitable CT images (e.g., contrast CT images, non-contrast CT images, etc.); magnetic resonance imaging (MRI) images; and/or any other suitable images.

Image data is preferably received at the router (e.g., directly, indirectly, etc.) from the imaging modality (e.g., scanner) at which the data was generated. Additionally or alternatively, image data or any other data can be received from any computing system associated with the healthcare facility's PACS server, any DICOM-compatible devices such as a DICOM router, or any other suitable computing system. The image data is preferably in the DICOM format but can additionally or alternatively include any other data format.

In addition to or alternative to image data, the data can include blood data, electronic medical record (EMR) data, unstructured EMR data, health level 7 (HL7) data, HL7 messages, clinical notes, or any other suitable data related to a patient's medical state, condition, or medical history.

The data preferably includes a set of one or more instances (e.g., images), which can be unorganized, organized (e.g., into a series, into a study, a sequential set of instances based on instance creation time, acquisition time, image position, instance number, unique identification (UID), other acquisition parameters or metadata tags, anatomical feature or location within body, etc.), complete, incomplete, randomly arranged, or otherwise arranged.

The data packet further preferably includes metadata associated with the set of images, such as, but not limited to, any or all of: one or more patient identifiers (e.g., name, identification number, UID, etc.), patient demographic information (e.g., age, race, sex, etc.), reason for presentation (e.g. presenting symptoms, medical severity score, etc.), patient history (e.g., prior scans, prior diagnosis, prior medical encounters, etc.), medical record (e.g. history of present illness, past medical history, allergies, medications, family history, social history, etc.), scan information, scan time, scan type (e.g., anatomical region being scanned, scanning modality, scanner identifier, etc.), number of images in scan, parameters related to scan acquisition (e.g., timestamps, dosage, gurney position, scanning protocol, contrast bolus protocol, etc.), image characteristics (e.g., slice thickness, instance number and positions, pixel spacing, total number of slices, etc.), or any other suitable information.

In some variations, S205 includes checking for a set of metadata and/or other image features, which functions to check for a set of inclusion criteria. In a set of specific examples, this includes checking for any or all of: a CTA scan of the head; an axial series of images; a slice thickness within a predetermined range (e.g., between 0.5 mm and 1 mm); an absence of missing slices; an alignment of instance numbers and/or positions; an age of the patient (e.g., above a predetermined threshold); consistent pixel spacing; and/or any other suitable inclusion criteria. S205 can additionally or alternatively include filtering images (e.g., images within a series, entire series, etc.) based on any or all associated metadata.

The method 200 can optionally further include transmitting any or all of the data packet to a computing system, such as a remote computing system, which functions to enable any or all of the subsequent processes to be performed at a remote computing system.

Each instance (e.g., image) of the dataset (e.g., image dataset) is preferably sent individually as it is generated at an imaging modality and/or received at a router, but additionally or alternatively, multiple instances can be sent together after a predetermined set (e.g., series, study, etc.) has been generated, after a predetermined interval of time has passed (e.g., instances sent every 10 seconds), upon the prompting of a medical professional, or at any other suitable time. Further additionally or alternatively, the order in which instances are sent to a remote computing system can depend one or more properties of those instances (e.g., metadata). Transmitting the data packet can be performed a single time or multiple times (e.g., after each instance is generated), and can include transmitting any or all of: all of the dataset (e.g., image dataset and metadata), a portion of the dataset (e.g., only image dataset, subset of image dataset and metadata, etc.), or any other information or additional information (e.g., supplementary information such as supplementary user information).

The data is preferably transmitted through a secure channel, further preferably through a channel providing error correction (e.g., over TCP/IP stack of $1^{st}$ point of care), but can alternatively be sent through any suitable channel.

Prior to transmitting data to a computing system, any or all of the following can be performed: encrypting any or all of the dataset (e.g., patient information) prior to transmitting to the remote computing system, removing information (e.g., sensitive information), supplementing the dataset with additional information (e.g., supplementary patient information, supplemental series of a study, etc.), compressing any or all of the dataset, or performing any other suitable process.

In preferred variations, for patients presenting with and/or potentially presenting with an aneurysm, the data packet includes a set of CTA DICOM images taken at a CT scanner, which are sent to a remote computing system for processing (e.g., as described below). Additionally or alternatively, images in any suitable format can be received from any suitable scanner and/or imaging system (e.g., MRI scanner, ultrasound system, X-Ray system, etc.).

4.2 Method—Preprocessing the Set of Images S210

The method 200 preferably includes preprocessing the set of images S210, which functions to prepare the images for subsequent process of the method.

S210 is preferably performed in response to and based on S205, but can additionally or alternatively be performed in response to any other processes, prior to one or more processes, in parallel with one or more processes, in absence of S215, and/or at any other times. Further additionally or alternatively, the method 200 can be performed in absence of S210.

S210 can optionally include organizing the set of images, such as based on one or more type of metadata associated with the images. This can function to enable any or all of: easier, more accurate, and/or quicker processing; the selection of one or more models and/or algorithms for processing (e.g., based on patient metadata such as age and/or gender); the determination of a $2^{nd}$ point of care, procedure, and/or specialist (e.g., based on metadata specifying $1^{st}$ point of care); resampling and/or otherwise preprocessing/processing the set of images; and/or can enable any other suitable actions. In variations where the set of images are sent to a remote computing system, the metadata can be read prior to transmitting to the remote computing system (e.g., at a virtual server coupled to the scanner and/or to a PACS system at the point of care), at the remote computing system, any combination, and/or at any other suitable times.

In a first set of variations, dimension metadata (e.g., spacing between pixels, spacing between slices, etc.) from the set of images are read and used to map and/or arrange the set of images in an array.

In a second set of variations additional or alternative to the first set, patient demographic metadata are read and used to determine and/or select a particular set of models, such as a set of models taking into account and/or trained based on any or all of these metadata.

S210 can optionally include converting the image slices into an array of intensities (e.g., Hounsfield unit [HU] values), which functions to represent the set of images with intensity values for further processing. Additionally or alternatively, the set of images can be converted into any other suitable arrays and/or types of information.

S210 can include checking for a set of exclusion criteria associated with the set of images and excluding the images from further processing in an event that any or all of the exclusion criteria are satisfied. The exclusion criteria preferably include criteria associated with intensity values of the set of images, such as voxels having an HU value above a predetermined threshold (e.g., 3000 HU, between 2800 HU and 3000 HU, between 2500 HU and 3000 HU, between 3000 HU and 3200 HU, between 3000 HU and 3500 HU, etc.), which can correspond to a metallic artifact (e.g., aneurysm clip). Additionally or alternatively, any or all of the exclusion criteria can be determined based on metadata (e.g., as described above in the inclusion criteria), and/or any other suitable information. Checking for exclusion criteria can additionally or alternatively be performed in S205 and/or in any other process of the method 200.

S210 preferably includes extracting regions and/or images of interest from the set of images, which functions to perform further processing only on relevant information. This can include any or all of: extracting only the images including the anatomy of interest (e.g., removing images below the head based on a fixed size threshold relative to the top of the scan); extracting soft matter (e.g., based on a set of HU value thresholds, based on a skull stripping process, etc.); extracting vessels; and/or otherwise extracting regions and/or images of interest.

In preferred variations, this includes cropping any or all of the set of images, which function to reduce a region of the images that is processed in subsequent processes of the method. The images can be cropped to any or all of: a predetermined size (e.g., based on a predetermined number of pixels, based on predetermined dimensions and/or area, etc.); an inclusion of a predetermined number and/or percentage of locations determined in a registration process (e.g., all locations, minimum area including all locations, at least 90% of all locations, a particular subset of locations, etc.); a predetermined size and inclusion of all locations (e.g., a predetermined size centered on the set of locations, a predetermined border extending past the outermost locations, etc.); and/or the images can be cropped in any other suitable ways. The images can all be cropped to the same size, can be cropped to different sizes, can be filtered and eliminated (e.g., upon not having any identified locations, upon having a number of locations below a threshold, etc.), and/or can be otherwise cropped or not cropped. The images can be cropped a single time throughout the method 200, multiple times throughout the method 200, and/or at any suitable times throughout the method 200.

In some variations, for instance, each of the set of images is first cropped (e.g., 220 mm cropped off the superior portion of the images) to remove portions not corresponding to brain.

S210 preferably includes clipping the set of images through a clipping transformation process, which functions to remove HU values irrelevant to the suspected condition (e.g., irrelevant to an aneurysm) from the set of images. The irrelevant HU values to be clipped can correspond to high HU values, low HU values, or both. In preferred variations, for instance, a first set of HU values below a predetermined threshold (e.g., between −500 and −520, less than −520, greater than −500, etc.) are clipped and a second set of HU values above a predetermined threshold (e.g., between 1000 and 1100, between woo and 1200, greater than 1200, less than 1000, etc.) are clipped.

S210 preferably includes normalizing the HU values of the set of images, which can function to enable optimal processing later in the method, enable comparisons to be made between multiple sets of images, and/or confer any other suitable function. The HU values can be normalized based on any or all of: a mean HU value from the set of images (e.g., after clipping), a median HU value, a standard deviation of the HU values, a predetermined HU value, and/or any other suitable value(s). In some variations, the HU values are normalized by subtracting the mean HU value and dividing by the standard deviation. Additionally or alternatively, the HU values can be otherwise normalized and/or not normalized.

In a first variation, S210 includes cropping the set of images to include the head region, clipping the set of images to remove relatively high and relatively low HU values, and normalizing the HU values of the images.

In a second variation, S210 includes cropping the set of images to include the head region, clipping the set of images to remove a skull from the images, and normalizing the HU values of the images.

Additionally or alternatively, S210 be performed in absence of any or all of these pre-processing processes.

Further additionally or alternatively, S210 can include any other suitable processes.

4.3 Method—Processing the Set of Images to Determine a Suspected Condition and/or Associated Features S220

The method includes processing the set of images to determine a suspected condition and/or associated features S220, which functions to identify a suspected condition in the set of images and to optionally determine one or more features associated with the suspected condition, any or all of which can be used in the determination and/or triggering of an action related to care of the patient (e.g., as described below).

S220 is preferably performed in response to and based on S210, but can additionally or alternatively be performed in response to any other processes (e.g., S205), in parallel with one or more processes, prior to one or more processes, and/or at any other times. Further additionally or alternatively, S220 can be performed in absence of S210, performed based on information other than that received in S210 and/or S205, multiple times during the method 200, and/or the method 200 can be performed in absence of S220.

The images are preferably processed based on a set of one or more trained models (e.g., CNNs, deep 3D convolutional neural networks, feed forward deep CNNs, etc.) which are preferably trained (e.g., based on supervised learning, based on unsupervised learning, based on a combination of supervised and unsupervised learning, etc.) to perform any or all of: detecting the presence of a potential aneurysm, determining its location, determining an approximate segmentation of the potential aneurysm, determining one or more scores (e.g., confidence score, likelihood score, probability, etc.) associated with the aneurysm, and/or determine any other information. Additionally or alternatively, the model(s) can be any or all of: configured to determine a portion of the outputs; configured to determine other outputs (e.g., a severity of a potential aneurysm, other metrics associated with the potential aneurysm, a specialist, a treatment option, etc.); be otherwise trained and/or structured (e.g., deep learning models other than deep CNNs); and/or any other models can be implemented to determine any suitable parameters.

S220 can optionally include resampling the images (e.g., pre-processed images, cropped images produced in S205, output images of S205, original images, etc.) to a higher image resolution (e.g., to the input resolution of the original scan, to a predetermined percentage of the input resolution of the original scan, etc.), which preferably functions to enable detection (e.g., fast detection, detection with reduced computing resources, etc.) of relatively small aneurysms (e.g., 1 mm in diameter or below, 1 mm or greater in diameter, between 1 mm and 3 mm in diameter, less than 5 mm in diameter, less than 4 mm in diameter, less than 3 mm in diameter, etc.). Additionally or alternatively, this can function to enable the performance of a registration process (e.g., as described below) and/or can perform any other function(s). In specific examples, for instance, this functions to provide a higher resolution to images which have been cropped to a smaller region. Additionally or alternatively, uncropped and/or any other images can be resampled. Further additionally or alternatively, S220 can be performed in absence of resampling the images.

The resolution to which the images are resampled to can be any or all of: predetermined, determined based on the resolution of the original scan, dynamically determined, and/or otherwise determined. In a set of preferred variations, the set of images, which have been cropped to include the head, clipped, and normalized, are resampled to a predetermined resolution (e.g., 1 mm, 0.5 mm, between 0.5 and 1.5 mm, 2 mm, less than 1 mm, greater than 1 mm, etc.) in all dimensions (e.g., each voxel dimension, each pixel dimension, etc.). The predetermined resolution is preferably associated with a minimum size of aneurysm (e.g., desired smallest size) for the method to detect, but can additionally or alternatively be associated with a maximum size of aneurysm for the method to detect, another size of aneurysm (e.g., average size, median size, etc.), and/or any other size. Additionally or alternatively, the images can be resampled according to any other parameters and/or desired dimensions. Further additionally or alternatively, the images can be processed without resampling, the images can be downsampled, and/or the images can be otherwise processed.

S220 further preferably includes a cropping process (reference cropping process) prior to a registration process described below (e.g., additional to a cropping in S210, in place of a cropping in S210, etc.), which functions to crop the resampled images in preparation for comparison/registration with an atlas image. The cropping process preferably includes a cropping in the z-axis (e.g., from the top of the head in the scan) and a cropping in the x-y plane (e.g., from the center of the scan), but can additionally or alternatively include any other suitable cropping and/or no cropping. In specific examples, the images are cropped to narrow in on an region associated with the Circle of Willis. Additionally or alternatively, the images can be otherwise suitably cropped, and/or S220 can be performed in absence of this and/or any other cropping processes.

S220 includes performing a registration process, which functions to identify and/or construct an anatomic (e.g., vasculature) region and/or a pathological region (e.g., region containing an aneurysm) of interest. This can additionally function to enable subsequent processes (e.g., segmentation processes) of the method and/or reduce the processing requirements of subsequent steps of the method (e.g., cropping to a region of interest).

For variations involving brain conditions (e.g., aneurysms), the registration process (e.g., through a set of neural networks) preferably identifies and outputs a predetermined set of brain locations (e.g., based on an atlas). The predetermined set of brain locations preferably includes arbitrary locations, but can additionally or alternatively include non-arbitrary (e.g., anatomically defined and/or categorized) locations, and/or any combination of arbitrary and non-arbitrary. The set of brain locations preferably includes a plurality of locations (e.g., greater than 500, between 500 and 520, between 500 and 550, between 500 and 600, greater than 600, between 200 and 500, less than 200, between 5 and 10, etc.), but can additionally or alternatively include any number of locations, multiple subsets of location, and/or any other suitable locations.

The registration process can additionally or alternatively include any or all of: rotating one or more images, translating one or images, scaling one or more images, and/or otherwise adjusting any or all of the images.

The registration process is preferably performed with a set of trained models (e.g., machine learning models, deep learning models, etc.), such as through a set of one or more neural networks. The set of neural networks preferably includes a set of one or more convolutional neural networks (CNNs) (e.g., deep CNNs, feed forward deep CNNs, etc.), further preferably CNNs with a U-Net and/or V-Net architecture. Additionally or alternatively, the set of neural networks can include CNNs with other architecture(s), non-convolutional neural networks, recurrent neural networks, recursive neural networks, and/or any other neural networks. Further additionally or alternatively, the registration process can be performed with any number of rule-based, programmed, and/or manual processes.

In a set of preferred variations (e.g., as described below), the registration process is performed with a neural network on a set of brain scans, which outputs a plurality of arbitrary brain locations (e.g., points) proximal to (e.g., located around, located within, partially overlapping with, fully overlapping with, encircling, etc.) the Circle of Willis, wherein the output effectively approximates the Circle of Willis. The plurality of locations can optionally be associated with and/or configured for any number of constraints. In some examples, for instance, to ensure that the key points collectively cover a large volume in the brain (e.g., above a predetermined threshold, for accuracy of the resulting points, etc.), a separation constraint can be implemented in the neural networks (e.g., with a loss function) which penalizes pairs of predicted key points which are too close to each other (e.g., below a predetermined distance threshold, below a predetermined distance threshold between 0-5 mm, below a predetermined distance threshold of between 1-2 mm, below a predetermined distance threshold of between 0.1 mm and 1 mm, etc.). Additionally or alternatively, any other constraints can be implemented and/or the key points can be identified in absence of constraints.

In specific examples, for instance, a neural network (e.g., deep CNN with U-Net architecture) identifies a set of points (equivalently referred to herein as key points) in one or more images (e.g., all images in the series, all images received in S220, a subset of images, a single most relevant image, etc.), wherein the key points preferably correspond to arbitrary points proximal to the Circle of Willis, but can additionally or alternatively include anatomically-meaningful key points. The key points preferably correspond to a predetermined, fixed number set of points (e.g., predetermined set of points in the reference images), but can additionally or alternatively include dynamically determined points and/or any combination. The number of key points is preferably configured to achieve a compromise between registration quality and computational load, but can additionally or alternatively be otherwise determined. The number of key points is further preferably configured to cover a relatively large volume of the brain, which can be enabled using a separation constraint, which functions to incorporate a term in a loss function which penalizes pairs of predicted key points that are relatively close to each other, but can additionally or alternatively be otherwise determined and/or configured.

Additionally or alternatively, any suitable key points can be selected in any suitable way.

The registration process further preferably includes comparing the set of images (e.g., cropped region) with a similar region in a reference atlas based on the set of locations (e.g., points) determined with the set of neural networks, which functions to determine (e.g., compute) a transformation to be applied to the set of images. In preferred variations, an affine transformation is computed, but additionally or alternatively, any other suitable transformation can be computed.

The transformation is preferably an affine transformation, which can be solved for using a least-squares regression applied between the key points of the images and the same number of key points of the atlas, which effectively registers the scan to the atlas. Additionally or alternatively, any or other suitable transformation can be computed in any suitable way.

The registration process preferably additionally includes applying the computed transformation (e.g., affine transformation) to the set of images, which functions to enable subsequent processes of the method to be accurately performed (e.g., anatomically correct aneurysm detected, location of aneurysm properly identified, etc.), such as a desired anatomical region to be accurately cropped. The set of images to which the transformation is applied is preferably the entire input scan received in S205 (e.g., without any cropped regions, without any preprocessing or processing, etc.) which functions perform the analysis on the original images. Additionally or alternatively, the transformation can be applied to any other set of images (e.g., images produced in S210, images produced in S220, etc.).

In response to the transformation, S220 can optionally include cropping the transformed images, which functions to narrow in on a region of interest for subsequent processes of the method 200. In preferred variations, a region around the Circle of Willis (e.g., region including the Circle of Willis in its entirety, a region including at least a portion of the Circle of Willis, etc.) is cropped from the transformed images. The cropping coordinates are preferably fixed and based on the location of the region of interest in the atlas, as the transformation has aligned these coordinates with those of the atlas. Additionally or alternatively, the cropping region can be dynamically determined (e.g., based on an identification of the Circle of Willis in the set of images, based on non-transformed images, etc.) and/or otherwise determined.

In a set of specific examples, a region containing the Circle of Willis having predetermined dimensions of (e.g., 114 mm×112 mm×128 mm) is cropped from the transformed input set of images. Additionally or alternatively, a smaller region can result from the cropping, a larger region can result from the cropping, and/or the cropping can be otherwise performed.

S220 can optionally include resampling the images after transforming and/or cropping the images (e.g., additional to the resampling performed above, in place of the resampling performed above, etc.), which can function to enable even smaller aneurysms to be accurately detected (e.g., based on the smaller cropped region). In a set of variations, the images are resampled to a resolution (e.g., voxel dimension) of 0.5 mm. Additionally or alternatively, the images can be resampled to a resolution greater than 0.5 mm, less than 0.5 mm, the images can be downsampled, and/or S220 can be performed without this resampling process.

S220 preferably includes segmenting the set of images, which functions to identify and isolate one or more aneurysms. The segmentation is preferably performed with a set of one or more trained models (e.g., machine learning models, deep learning models, neural networks, etc.) configured to detect regions of the images associated with an aneurysm (e.g., hyperattenuated regions, regions having a particular shape/morphology, regions in a particular anatomical location, etc.). The set of trained models can include any or all of those described above, be different than any or all of those described above, be the same (e.g., part of) any or all of those described above, and/or be of any other type(s). In specific examples, for instance, the segmentation is performed with a feed-forward deep CNN (e.g., with a U-Net architecture). Additionally or alternatively, any or all of the segmentation process can be performed with any other suitable models (e.g., trained models, rule-based models, programmed models, etc.) having any suitable architecture (e.g., V-nets, U-nets, etc.). In preferred variations, a feed-forward deep CNN with a U-Net architecture trained to segment hyper-attenuated regions consisted with aneurysms is implemented.

The models are preferably trained based on manual segmentations of scans positive for aneurysms and scans negative for aneurysms, further preferably with a cross-entropy loss function (e.g., computed over all voxels). Additionally or alternatively, the deep learning models can be trained based on any or all of: augmented data (e.g., using any or all of: random rotations, scaling, translation, elastic deformation, and additions of Gaussian noise; etc.), but can additionally or alternatively be trained with any suitable data and/or tools.

The deep learning models preferably receive a transformed, cropped region (e.g., as described above) of the set of images as an input, but can additionally or alternatively receive any other information (e.g., a preprocessed set of images, a processed set of images, etc.).

The segmentation preferably produces as an output a 3D array containing probability values between 0 and 1 for each voxel, the probability corresponding to the likelihood that each voxel within the scan represents a portion of an aneurysm, which functions to determine a suspected aneurysm. The probability values are further preferably then summed, wherein the summed value is compared with a threshold and used to make a determination of whether or not the scan contains an aneurysm. The threshold is preferably selected to establish both a relatively high sensitivity and a relatively high specificity (e.g., both above 91%, both above 90%, etc.), but can additionally or alternatively be otherwise selected. In preferred variations, the threshold is between 15 and 25 (e.g., 20, 18, 22, etc.), but can additionally or alternatively be 15 or less (e.g., 10, 12, etc.), 25 or greater (e.g., 26, 28, 30, etc.), or have any other suitable value. Further additionally or alternatively, an upper limit threshold can be used, the segmentation can be otherwise performed, and/or any other thresholds or algorithms can be used.

Figure 12:
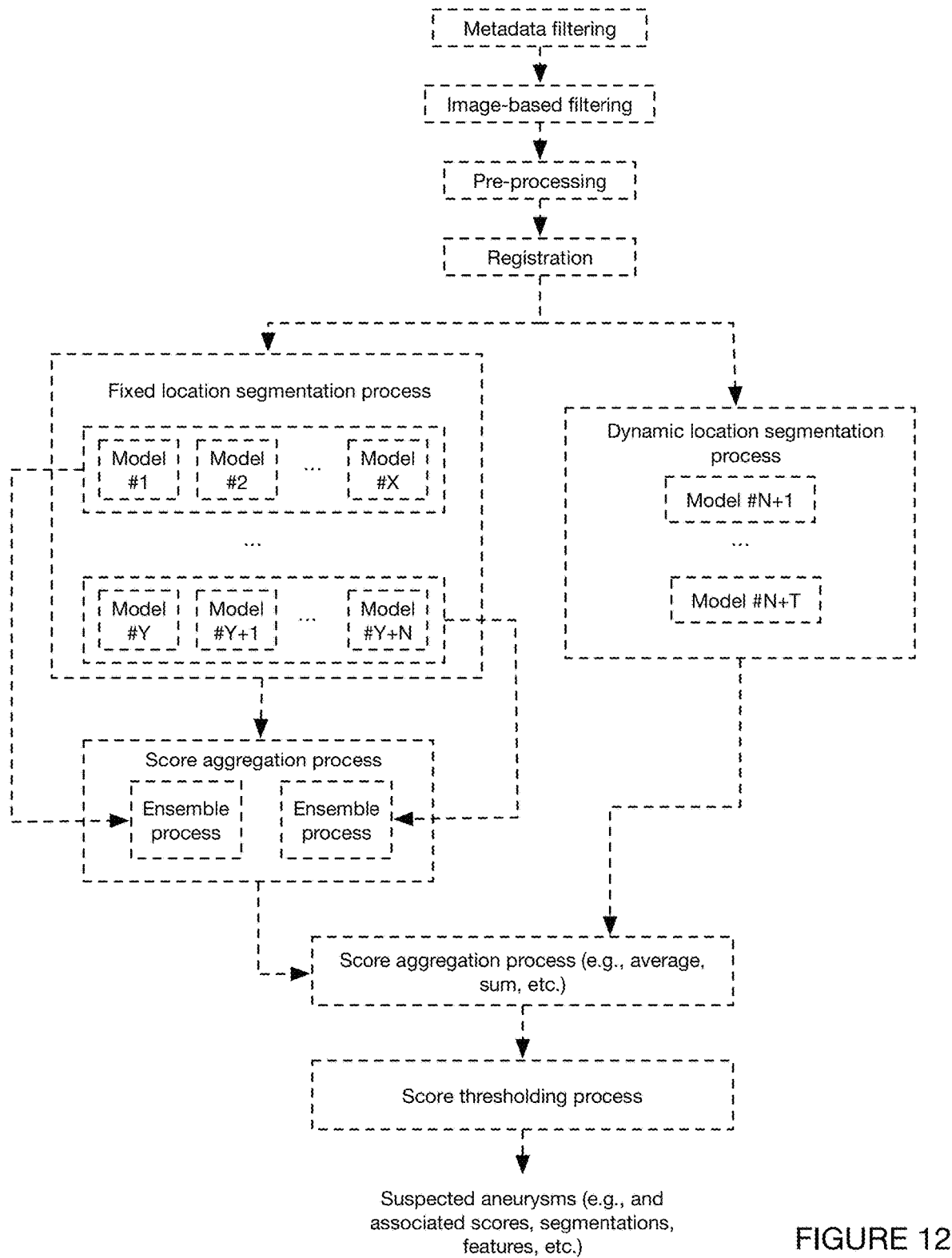
FIG. 12 depicts a variation of a method for the computer-aided detection of one or more suspected aneurysms.

In some variations (e.g., as shown in FIG. 12), the segmentation process includes a dynamic location segmentation process (equivalently referred to herein as a multi-stage segmentation process), wherein the dynamic location segmentation process involves predicting aneurysms within the set of images and refining, in multiple stages, these predictions.

The dynamic location segmentation process preferably includes predicting the locations of one or more aneurysms in the set of images (e.g., entire region resulting from pre-processing and/or registration) with a set of bounding boxes (e.g., 3D bounding boxes including sets of voxels, 2D bounding boxes including sets of pixels, etc.), wherein each bounding box includes a predicted segmentation of an aneurysm.

The dynamic location segmentation process is preferably an instance segmentation method performed with a set of multiple neural networks, which can be any or all of: the same architecture (e.g., with different weights, the same weights, etc.), different architectures, and/or any combination, but can additionally or alternatively be in the form of any other segmentation type. A first neural network (e.g., feed-forward deep CNN, other CNN, non-CNN, etc.) is preferably applied to the images and/or a region of the set of images (e.g., wherein each of a set of regions is processed independently and the results merged), which produces a feature map defining a set of proposals for potential detected aneurysms, wherein each proposal preferably includes a score and bounding box. Each of these proposals is then progressively refined through a second set of neural networks (e.g., same architecture, different architecture, etc.) performed in a set of multiple stages (e.g., with different weights at each stage). At each stage, the feature map produced by the prior stage is processed to predict a set of bounding boxes, thereby refining the bounding boxes predicted at the prior stage. Each stage of refinement preferably results in scores which are higher in accuracy than the prior stage's scores, and fewer proposals are needed to keep false negatives low. Decreasing the number of proposals allows for using a wider and/or deeper neural network to process them, as due to limited to computational resources, there is a tradeoff between the number of proposals and the size (e.g., width and depth) of the neural network. Additionally or alternatively, the neural networks can be otherwise configured relative to the stage of implementation (e.g., decreasing size, same size, etc.). The last stage preferably produces as an output a segmentation mask for the set of images, wherein the segmentation mask indicates a set of scores associated with predicted aneurysms remaining after the final stage. Determining this segmentation mask can optionally include checking the scores of the segmentation mask with a set of thresholds (e.g., where a predicted aneurysm associated with a summed score below a threshold can be removed from consideration). Additionally or alternatively, any other output(s) can be produced.

The second set of neural networks preferably includes at least 2 stages (e.g., 2, 3, 4, between 2-10, greater than 10, etc.), but can additionally or alternatively include any number of stages.

In specific examples of the dynamic location segmentation process, a feed-forward deep CNN with a U-Net architecture is used for each of the first neural network and the second set of neural networks. Additionally or alternatively, any other neural networks (e.g., other CNNs, other architectures, etc.) or combination can be used.

Specific Examples: Feed-Forward Deep CNN with U-Net Architecture

In additional or alternative variations (e.g., as shown in FIG. 12), the segmentation process includes a fixed location segmentation process (equivalently referred to herein as a single stage segmentation process), wherein the fixed location segmentation process involves checking for aneurysms in a predetermined set of most likely locations. The locations are preferably located relative to the Circle of Willis, but can additionally or alternatively be otherwise defined and/or located. In specific examples, for instance, a set of predetermined regions (e.g., between 1-10 regions, between 5-8 regions, 5, regions, 6 regions, 7 regions, between 5-10 regions, between 10-20 regions, greater than 20 regions, etc.) is cropped from the set of images and each of the predetermined regions processed with a neural network, wherein the set of predetermined regions has been found to contain more than a predetermined percentage (e.g., 90%, 95%, 99%, between 90-100%, etc.) of aneurysms (e.g., in training data, in literature, in an aggregated dataset, etc.). Additionally or alternatively, the set of predetermined regions can be otherwise selected.

Each of the predetermined regions is preferably processed with a CNN, further preferably a feed-forward deep CNN with a U-Net architecture (e.g., as described above). Additionally or alternatively, any other neural networks can be used, any or all of the regions can be determined with different neural networks, and/or the regions can be otherwise processed. In specific examples, each of the predetermined regions is processed with a feed-forward deep CNN, wherein each of these CNNs shares network weights but has a region-specific bias term learned for each region. Additionally or alternatively, the neural networks can be different, have different weights, not have any region-specific terms, and/or be otherwise defined.

The outputs of the fixed location segmentation process can optionally be combined (e.g., aggregated, summed, compared to select the highest scores, compared with thresholds, etc.), such as in an ensemble process (e.g., pixel-wise ensemble process, voxel-wise ensemble process, etc.).

Additionally or alternatively, in variations in which both the dynamic and fixed location segmentation processes are performed (e.g., in series, in parallel, etc.), the scores from these processes can optionally be aggregated (e.g., summed based on location, compared and used to determine a maximum score for each location, aggregated based on an equation, etc.). Additionally or alternatively, they can be individually maintained (e.g., and individually compared with a set of thresholds) and/or any combination.

In variations including multiple suspected aneurysms, the scores for each aneurysm can be any or all of: independently determined, combined (e.g., summed together), used to calculate a combined score, and/or otherwise calculated and/or used. Additionally or alternatively, in variations including multiple processes (e.g., multiple independent processes) for detecting aneurysms (e.g., dynamic location segmentation process and fixed location segmentation process), the scores for the detected aneurysms can be aggregated and/or otherwise processed (e.g., summed, combined according to an equation, compared with a set of machine learning models, compared to determine highest scores, compared with a set of thresholds) to determine a final set of scores.

Any or all of the scores (e.g., as described above) are preferably compared with a set of one or more thresholds (e.g., as described above), wherein in an event that scores exceed the threshold(s), a suspected aneurysm is detected/confirmed (e.g., and used to trigger one or more actions). The scores compared with the threshold can be any or all of: associated with a single suspected aneurysm, associated with a multiple suspected aneurysms (e.g., aggregated scores), associated with a particular region of the set of images, associated with a particular segmentation process (e.g., dynamic location segmentation process, fixed location segmentation process, etc.), associated with multiple segmentation processes (e.g., aggregated scores from fixed location and dynamic location segmentation processes), and/or any other scores. Additional or alternative to seeing if the scores exceed a threshold, the method can include seeing if the scores are below a threshold (e.g., for further investigation), comparing scores with a decision tree and/or lookup table, processing the scores with a model and/or algorithm and/or equation, and/or otherwise processing and/or interpreting the scores.

Any or all of the set of trained models can optionally additionally or alternatively be used to determine features and/or parameters associated with a suspected aneurysm or other suspected condition, such as, but not limited to, any or all of: size features (e.g., aneurysm diameter, aneurysm cross-sectional area, aneurysm volume, number of voxels making up aneurysm, number of pixels making up aneurysm, etc.); temporal features (e.g., predicted time until rupture, predicted time since rupture, etc.); one or more supplementary scores (e.g., risk score associated with aneurysm, severity score associated with aneurysm, etc.); and/or any other features. Trained models (e.g., as described above, as described below, etc.) can additionally or alternatively be used to determine one or more actions (e.g., as described below), such as any or all of: a treatment option (e.g., procedure type, aneurysm coil size, etc.); a recipient to notify (e.g., particular specialist) based on a suspected aneurysm; a recommended path with which to access the aneurysm; and/or can perform any other suitable actions.

Further additionally or alternatively, any or all of the actions, associated features, and/or the detection of the suspected condition can be performed in absence of trained models, with a combination of trained models and untrained tools (e.g., rule-based models, programmed models, decision trees, manual input and/or manual processes, lookup tables, algorithms, equations, etc.), and/or any other tools.

In a first variation, S220 includes resampling the images; cropping the images; registering the images through the computation and application of a transformation, wherein the transformation is based on a set of key points determined based on a deep learning model; cropping the images based on the transformation; resampling the cropped image to a higher resolution; segmenting the cropped images to identify one or more aneurysms; calculating a score based on the segmentation; and comparing the score with a predetermined threshold, wherein if the score is above the predetermined threshold, a suspected aneurysm is determined.

In a first specific example of this variation, the segmentation process includes a dynamic location segmentation process which uses a set of neural networks (e.g., feed-forward deep CNNs with a U-Net architecture) to process the set of images in a set of multiple stages (e.g., 4 stages, 3 stages, 5 stages, etc.), wherein each subsequent stage refines the prediction of an aneurysm in the set of images, ultimately resulting in a set of scores associated with the predicted aneurysm(s). These scores can then be any or all of aggregated and compared with a threshold.

In a second specific example of this variation, the segmentation process includes a fixed location segmentation process, which analyzes a predetermined set of regions from the set of images with a neural network (e.g., feed-forward deep CNN with a U-Net architecture) to determine a set of scores associated with a predicted likelihood of an aneurysm being predicted in each region (e.g., in the form of a segmentation). These scores can be then any or all of aggregated and compared with a threshold.

In a third specific example of this variation, the segmentation process includes both a dynamic location segmentation process (e.g., as described above) and a fixed location segmentation process (e.g., as described below), wherein the scores produced from these processes can be aggregated and/or compared with one or more thresholds to determine a final set of predicted aneurysms and any or all of: an associated set of scores, associated segmentations, and/or any other information.

Additionally or alternatively, S220 can include any other suitable processes.

4.4 Method—Triggering an Action Based on the Suspected Condition and/or Associated Features S230

The method 200 can include triggering an action based on the suspected condition and/or associated features S230, which functions to determine and/or provide care for the patient based on the suspected condition and/or its associated features determined in S220. Additionally or alternatively, S230 can function to enable any or all of: faster treatment for the patient (e.g., in an event of a detected aneurysm, in an event of a detected critical aneurysm, etc.); better treatment for the patient (e.g., through the selection of an optimal surgical device, through the selection of the most appropriate treatment, through an automated path planning process to reach the aneurysm in a surgical intervention, etc.); better long-term treatment for the patient (e.g., automated follow-up and/or scheduling of follow-up imaging); and/or any other improved outcomes.

S230 is preferably performed in response to and based on S220, but can additionally or alternatively be performed in response to another process, in response to a trigger, in parallel with other processes of the method, prior to any other processes of the method, and/or at any other times. Further additionally or alternatively, S230 can be performed multiple times during the method 200, S230 can be performed in absence of S220, and/or the method 200 can be performed in absence of S230.

4.5 Method—Determining a Recipient Based on the Suspected Condition S232

S230 can optionally include, in an event that the condition (e.g., aneurysm) is suspected, determining a recipient based on the suspected condition S232, which functions to facilitate the treatment (e.g., triage, acceptance into a clinical trial, etc.) of the patient.

S232 can additionally, alternatively, and/or equivalently include determining a treatment option, preferably in the event that a condition is detected (e.g., based on a comparison with a threshold, based on a binary presence, etc.) but can additionally or alternatively determine a treatment option when a condition is not detected, when an analysis is inconclusive, or in any suitable scenario. S232 can function to match the patient with a specialist, initiate the transfer of a patient to a $2^{nd}$ point of care (e.g., specialist facility), initiate the transfer of a specialist to a $1^{st}$ point of care, initiate treatment of a patient (e.g., surgery, stent placement, etc.) within the $1^{st}$ point of care, initiate the matching of a patient to a clinical trial, schedule or tentatively schedule one or more procedures, or perform any other suitable function. In some variations, the treatment option is a $2^{nd}$ point of care, wherein it is determined (e.g., suggested, assigned, etc.) that the patient should be treated at the $2^{nd}$ point of care. Additionally or alternatively, the treatment option can be a procedure (e.g., surgical procedure, surgical clipping, mechanical thrombectomy, placement of an aneurysm coil, placement of a stent, retrieval of a thrombus, stereotactic radiosurgery, etc.), treatment, recovery plan (e.g., physical therapy, speech therapy, etc.), or any other suitable treatment.

The recipient and/or treatment is preferably determined based on a parameter determined from the data packet (e.g., binary presence of a condition, comparison of a parameter with a threshold, etc.), but can additionally or alternatively be determined based on additional data, such as patient information (e.g., demographic information, patient history, patient treatment preferences, etc.), input from one or more individuals (e.g., power of attorney, attending physician, emergency physician, etc.), a consensus reached by multiple recipients of a notification (e.g., majority of members of a care team, all members of a care team, etc.), or any other suitable information.

S232 is preferably at least partially performed with software operating at the remote computing system (e.g., remote server) but can additionally or alternatively be performed at a remote computing system separate from a previous remote computing system, a local computing system (e.g., local server, virtual machine coupled to healthcare facility server, computing system connected to a PACS server), or at any other location.

S232 is preferably performed after a patient condition has been determined during the method 200. Additionally or alternatively, S232 can be performed after a patient condition has been determined in an alternative workflow (e.g., at the $1^{st}$ point of care, at a radiologist workstation during a standard radiology workflow, in the case of a false negative, etc.), prior to or absent the determination of a patient condition (e.g., based on an input from a healthcare worker at the remote computing system, when patient is admitted to $1^{st}$ point of care, etc.), multiple times throughout the method (e.g., after a first treatment option fails, after a first specialist is unresponsive, such as after a threshold amount of time, such as 30 seconds, 1 minute, 2 minutes, etc.), or at any other time during the method.

S232 preferably determines the recipient and/or treatment option with a lookup table located in a database accessible at remote computing system (e.g., cloud-computing system). Additionally or alternatively, a lookup table can be stored at a healthcare facility computing system (e.g., PACS server), in storage at a user device, or at any other location.

In other variations, the recipient and/or treatment option can be determined based on one or more algorithms (e.g., predictive algorithm, trained algorithm, etc.), one or more individuals (e.g., specialist, care team, clinical trial coordinator, etc.), a decision support tool, a decision tree, a set of mappings, a model (e.g., deep learning model), or through any other process or tool.

The lookup table preferably correlates a $2^{nd}$ point-of-care (e.g., healthcare facility, hub, physician, specialist, neurointerventionist, etc.), further preferably a specialist or contact (e.g., administrative worker, emergency room physician, etc.), with a patient condition (e.g., presence of an ICH, presence of an LVO, presence of a pathology, severity, etc.), but can additionally or alternatively correlate any treatment option with the patient condition. The lookup table can further additionally or alternatively correlate a treatment option with supplementary information (e.g., patient history, demographic information, heuristic information, etc.).

The recipient (e.g., healthcare provider, neuro-interventional specialist, principal investigator, stroke care team member, principal investigator, clinical trial enrollment committee, etc.), equivalently referred to herein as a contact, is preferably a healthcare worker, but can additionally or alternatively be any individual associated with the treatment of the patient and/or be associated with any healthcare facility (e.g., prior healthcare facility of patient, current healthcare facility, recommended healthcare facility) related to the patient. The contact is further preferably a specialist (e.g., neuro-interventional specialist, neurosurgeon, neurovascular surgeon, general surgeon, cardiac specialist, etc.) but can additionally or alternatively include an administrative worker associated with a specialist, multiple points of contact (e.g., ranked order, group, etc.), or any other suitable individual or group of individuals. The contact is preferably associated with a hub facility, wherein the hub facility is determined as an option for second point of care, but can additionally or alternatively be associated with a spoke facility (e.g., current facility, future facility option, etc.), an individual with a relation to the patient (e.g., family member, employer, friend, acquaintance, emergency contact, etc.), or any other suitable individual or entity (e.g., employer, insurance company, etc.). Additionally or alternatively, the contact can be an individual associated with a clinical trial (e.g., principal investigator at a $1^{st}$ point of care, principal investigator at a $2^{nd}$ point of care, approval/enrollment committee to approve a patient for a clinical trial, etc.), and/or any other suitable individual.

The lookup table is preferably determined based on multiple types of information, such as, but not limited to: location information (e.g., location of a $1^{st}$ point of care, location of a $2^{nd}$ point of care, distance between points of care, etc.), temporal information (e.g., time of transit between points of care, time passed since patient presented at $1^{st}$ point of care, etc.), features of condition (e.g., size of occlusion, severity of condition, etc.), patient demographics (e.g., age, general health, history, etc.), specialist information (e.g., schedule, On-call times, historic response time, skill level, years of experience, specialty procedures, historic success or procedures, etc.), healthcare facility information (e.g., current number of patients, available beds, available machines, etc.), but can additionally or alternatively be determined based on a single type of information or in any other suitable way. Information can be actual, estimated, predicted, or otherwise determined or collected.

S232 can include, for instance, any or all of: matching the patient with a specialist, initiating the transfer of a patient to a $2^{nd}$ point of care (e.g., specialist facility), initiate the transfer of a specialist to a $1^{st}$ point of care, initiate treatment of a patient (e.g., surgery, stent placement, mechanical thrombectomy, etc.) within the $1^{st}$ point of care, initiating the matching of a patient to a clinical trial, or performing any other suitable function. In some variations, the treatment option is a $2^{nd}$ point of care, wherein it is determined (e.g., suggested, assigned, etc.) that the patient should be treated at the $2^{nd}$ point of care. Additionally or alternatively, the treatment option can be a procedure (e.g., surgical procedure, surgical clipping, mechanical thrombectomy, place-ment of an aneurysm coil, placement of a stent, retrieval of a thrombus, stereotactic radiosurgery, etc.), treatment (e.g., tissue plasminogen activator (TPA), pain killer, blood thinner, etc.), recovery plan (e.g., physical therapy, speech therapy, etc.), or any other suitable treatment.

4.6 Method—Preparing a Data Packet for Transfer S234

S230 can optionally additionally or alternatively include preparing a data packet for transfer S234, which functions to produce a compressed data packet, partially or fully anonymize a data packet (e.g., to comply with patient privacy guidelines, to comply with Health Insurance Portability and Accountability Act (HIPAA) regulations, to comply with General Data Protection Regulation (GDRP) protocols, etc.), minimize the time to transfer a data packet, annotate one or more images, or perform any other suitable function. Additionally or alternatively, any or all of a data packet previously described can be transferred.

The data packet is preferably transferred (e.g., once when data packet is generated, after a predetermined delay, etc.) to a contact, further preferably a specialist (e.g., associated with a $2^{nd}$ point of care, located at the $1^{st}$ point of care, etc.), but can additionally or alternatively be sent to another healthcare facility worker (e.g., at $1^{st}$ point of care, radiologist, etc.), an individual (e.g., relative, patient, etc.), a healthcare facility computing system (e.g., workstation), a server or database (e.g., PACS server), or to any other suitable location.

S234 preferably includes compressing a set of images (e.g., series), but can additionally or alternatively leave the set of images uncompressed, compress a partial set of images (e.g., a subset depicting the condition), or compress any other part of a data packet. Compressing the data packet functions to enable the data packet to be sent to, received at, and viewed on a user device, such as a mobile device. Compressing the data packet can include any or all of: removing a particular image region (e.g., region corresponding to air, region corresponding to hard matter, region without contrast dye, irrelevant anatomical region, etc.), thresholding of voxel values (e.g., all values below a predetermined threshold are set to a fixed value, all values above a predetermined threshold are set to a fixed value, all values below −500 HU are set to −500, all voxel values corresponding to a particular region are set to a fixed value, all voxels corresponding to air are set to a predetermined fixed value, etc.), reducing a size of each image (e.g., scale image size by factor of 0.9, scale image size by factor of 0.7, scale image size by factor of 0.5, scale image size by a factor between 0.1 and 0.9, reduce image size by a factor of 4, etc.), or through any other compression method.

In one variation, the reduction in size of a set of images can be determined based on one or more memory constraints of the receiving device (e.g., user device, mobile device, etc.).

In some variations, such as those involving a patient presenting with a brain condition (e.g., aneurysm, ICH, LVO), the images taken at an imaging modality (e.g., CT scanner) are compressed by determining an approximate or exact region in each image corresponding to air (e.g., based on HU value, based on location, based on volume, etc.) and setting the air region (e.g., voxels corresponding to the air region, pixels corresponding to the air region, etc.) to have a fixed value. Additionally or alternatively, any non-critical region (e.g., bone, unaffected region, etc.) or other region can be altered (e.g., set to a fixed value, removed, etc.)

during the compression. In a specific example, for instance, a set of voxels corresponding to air are set to all have a common fixed value (e.g., an upper limit value, a lower limit value, a value between 0 and 1, a predetermined value, etc.).

In some variations, S234 includes identifying an optimal visualization to be transmitted (e.g., from a remote computing system) and received (e.g., at a user device), which functions to prepare an optimal output for a $2^{nd}$ point of care (e.g., specialist), reduce the time required to review the data packet, bring attention to the most relevant image data, or to effect any other suitable outcome.

In some variations, this involves a reverse registration process. In a specific example, for instance, this is done through maximum intensity projection (MIP), where an optimal range of instances is determined based on which images contain the largest percentage of the segmented anatomical region of interest in a MIP image.

Additionally or alternatively, S234 can include removing and/or altering (e.g., encrypting) metadata or any unnecessary, private, confidential, or sensitive information from the data packet. In some variations, patient information (e.g., patient-identifiable information) is removed from the data packet in order to comply with regulatory guidelines. In other variations, all metadata are extracted and removed from the data packet.

S234 can optionally include annotating one or more images in the data packet, which can function to draw attention to one or more features of the images, help a specialist or other recipient easily and efficiently assess the images, and/or perform any other suitable functions.

Annotating the images can optionally include adding (e.g., assigning, overlaying, etc.) one or more visual indicators (e.g., labels, text, arrows, highlighted or colored regions, measurements, etc.) to one or more images. The incorporation of the visual indicators can be determined based on any or all of: the suspected condition (e.g., type of visual indicators designated for the condition based on a lookup table), one or more thresholds (e.g., size thresholds), features of the suspected condition/pathology (e.g., location of hemorrhage within brain), preferences (e.g., specialist preferences, point of care preferences, etc.), guidelines (e.g., patient privacy guidelines), scores (e.g., risk score, severity score, etc.), and/or any other suitable information.

Images can additionally or alternatively be annotated with one or more metrics, such as one or more parameters (e.g., size as described above); scores (e.g., a clinical score, a severity score, etc.); instructions (e.g., recommended intervention); and/or any other suitable information.

Additionally or alternatively to being annotated on an image, any or all of the annotations can be provided in a separate notification, such as a message, document, and/or provided in any other suitable way.

The annotations are preferably determined automatically (e.g., at a remote computing system implementing the deep learning models, at a client application, at a mobile device executing a client application, etc.), but can additionally or alternatively be determined manually, verified manually, or otherwise determined.

S234 can optionally include prescribing a subset of images to be viewed by the recipient and/or an order in which images should be viewed (e.g., the particular image shown first to the recipient upon opening a client application in response to receiving a notification, the image shown in the thumbnail of a notification, the only image or subset of images sent, etc.). This can include, for instance, selecting the image or images indicating the suspected condition (e.g., all slices containing the suspected condition, a single slice containing the suspected condition, the slice containing the largest cross section of a suspected condition, the slice containing an important or critical feature of the suspected condition, etc.) for viewing by the recipient. In specific examples, the recipient (e.g., specialist) is sent a notification wherein when the recipient opens the notification on a device (e.g., mobile device), the image corresponding to the suspected condition is shown first (and optionally corresponds to a thumbnail image shown to the recipient in the notification).

The notification(s) and/or image(s) provided to a recipient are preferably provided within a threshold time period from the time in which the patient is imaged (e.g., 15 minutes, between 10 and 15 minutes, 10 minutes, 9 minutes, 8 minutes, 7 minutes, 6 minutes, 5 minutes, 3 minutes, 2 minutes, 1 minute, etc.), but can additionally or alternatively be provided in another suitable time frame (e.g., greater than 15 minutes), prior to a next action in the standard of care (e.g., prior to a decision is made by a radiologist in a parallel workflow), and/or at any other time(s).

In some variations, S234 includes storing a dataset (e.g., at a remote server, at a local server, at a PACS server, etc.). In one example, metadata are extracted from the image data and stored separately from image data in a relational database. In another example, any or all of the data packet are stored (e.g., temporarily, permanently, etc.) to be used in one or more future analytics processes, which can function to improve the method, better match patients with suitable treatment options, or for any other suitable purpose.

S234 can optionally include applying a low bandwidth implementation process, which can function to reduce the time until a specialist receives a first piece of data or data packet (e.g., an incomplete series, incomplete study, single instance, single image, optimal image, image showing occlusion, etc.), reduce the processing required to inform a specialist of a potential patient condition, reduce the amount of data required to be reviewed by a specialist, reduce the amount of data being transmitted from a remote computing system to a mobile device, or perform any other suitable function. The low bandwidth implementation process can include any or all of: organizing (e.g., chunking) data (e.g., chunking a series of images based on anatomical region), reordering data (e.g., reordering slices in a CT series), transmitting a portion (e.g., single image, single slice, etc.) of a data packet (e.g., series, study, set of images, etc.) to a device (e.g., user device, mobile device, healthcare facility workstation, computer, etc.), sending the rest of the data packet (e.g., only in response to a request, after a predetermined time has passed, once the data packet has been fully processed, etc.), or any other process. In a specific example, for instance, the image data (e.g., slices) received at a remote computing system from a scanner are chunked, reordered, and a subset of slices (e.g., a single slice) is sent to the device associated with a specialist (e.g., prior to sending a remaining set of slices, in absence of sending a remaining set of slices, etc.).

In some variations, S234 includes implementing a buffering protocol, which enables a recipient (e.g., specialist) to start viewing images (e.g., on a mobile device) prior to all of the images being loaded at the device (e.g., user device, mobile device, etc.) at which the recipient is viewing images. Additionally or alternatively, the buffering protocol can include transmitting images to the recipient in batches, annotating images in batches, or otherwise implementing a buffering protocol.

Additionally or alternatively, S234 can include any other suitable steps performed in any suitable order.

The method can additionally or alternatively include any other suitable sub-steps for preparing the data packet.

In a first set of variations, S234 includes determining a subset of one or more images conveying information related to a suspected patient condition (e.g., showing the presence of the condition, showing the largest region of the condition, showing a particular feature of the condition, etc.); optionally annotating the images (e.g., to point out the condition); and preparing a notification to be sent to the specialist, wherein the notification instructs the specialist to view at least the subset of images and optionally includes a thumbnail depicting one of the set of images which the specialist can view prior to viewing the images.

4.7 Method—Transmitting Information to a Device Associated with the Recipient S236

S230 can optionally additionally or alternatively include transmitting information to a device S236, which functions to convey information to recipient of the device and to receive one or more inputs from the recipient.

The device is preferably associated with (e.g., owned by, belonging to, accessible by, etc.) a specialist or other individual associated with the $2^{nd}$ point of care, but can additionally or alternatively be associated with an individual or computing system at the $1^{st}$ point of care, the patient, or any other suitable individual or system.

In one variation, the device is a personal mobile phone of a specialist. In another variation, the device is a workstation at a healthcare facility (e.g., first point of care, second point of care, etc.).

In some variations, information is sent to multiple members (e.g., all members) of a care team or clinical trial team, such as the care team who is treating, may treat the patient, or and/or will treat the patient. This can enable the care team members to do any or all of: make a decision together (e.g., transfer decision, treatment decision, etc.); communicate together (e.g., through the client application); and/or perform any other function.

The information preferably includes a data packet, further preferably the data packet prepared in S234. Additionally or alternatively, the information can include a subset of a data packet, the original data packet, any other image data set, or any other suitable data. The information further preferably includes a notification, wherein the notification prompts the individual to review the data packet at the device (e.g., a message reciting "urgent: please review!"). The notification can optionally include a thumbnail with a selected image (e.g., image indicating patient condition), which a recipient can view quickly, such as prior to the recipient unlocking device to which the notification is sent. Additionally or alternatively, the notification can prompt the individual to review data (e.g., original data packet, uncompressed images, etc.) at a separate device, such as a workstation in a healthcare facility, a PACS server, or any other location. Further additionally or alternatively, the notification can include any suitable information, such as, but not limited to: instructions (e.g., for treating patient, directions for reaching a healthcare facility), contact information (e.g., for emergency physician at first point of care, administrative assistant, etc.), patient information (e.g., patient history), or any other suitable information.

The notification preferably includes an SMS text message but can additionally or alternatively include a message through a client application (e.g., as described above, image viewing application, medical imaging application, etc.), an email message (e.g., de-identified email), audio notification or message (e.g., recording sent to mobile phone), push notification, phone call, a notification through a medical platform (e.g., PACS, EHR, EMR, healthcare facility database, etc.), pager, or any other suitable notification.

One or more features of a notification can optionally convey a severity of the patient condition and/or an urgency of receiving a response from a recipient, which can function to adequately alert the recipient and properly prioritize care of the patient (e.g., relative to other patients). In specific examples, for instance, an audio cue associated with a notification indicates an urgency of treating a patient, so that a recipient of the message knows to immediately review the images and triage the patient.

The information is preferably sent to the device through a client application executing on the user device but can additionally or alternatively be sent through a messaging platform, web browser, or other platform. In some variations, the information is sent to all devices (e.g., mobile phone, smart watch, laptop, tablet, workstation, etc.) associated with the recipient (e.g., specialist), such as all devices executing the client application associated with the recipient, which functions to increase the immediacy in which the recipient is notified.

S234 can optionally include preparing a notification to be sent to a device (e.g., user device, mobile device, etc.) associated with a recipient (e.g., a specialist), wherein the notification includes a thumbnail indicating a selected image (e.g., compressed image showing a suspected condition), along with a message instructing the recipient to review the images in a client application, and optionally the original images at a workstation afterward. In a first set of specific examples, upon detection that a read receipt has not been received (e.g., at the remote computing system) in a predetermined amount of time (e.g., 30 seconds, 1 minute, 2 minutes, between 0 seconds and 2 minutes, 3 minutes, between 2 minutes and 3 minutes, 5 minutes, greater than 5 minutes, less than 10 minutes, etc.), a second notification is transmitted to a second recipient (e.g., a second specialist). In a second set of specific examples, sending the notification further triggers and/or enables communication to be established among multiple members of a care team (e.g., a stroke team), such as through a messaging component of the client application, wherein the images can be viewed and discussed among the care team members. In a third set of specific examples, a notification is sent to specialist on a mobile device of the specialist, compressed images are previewed on the specialist mobile device, and the specialist is notified as being responsible for viewing non-compressed images on a diagnostic viewer and engaging in appropriate patient evaluation and relevant discussion with a treating physician before making care-related decisions or requests.

Figure 6:
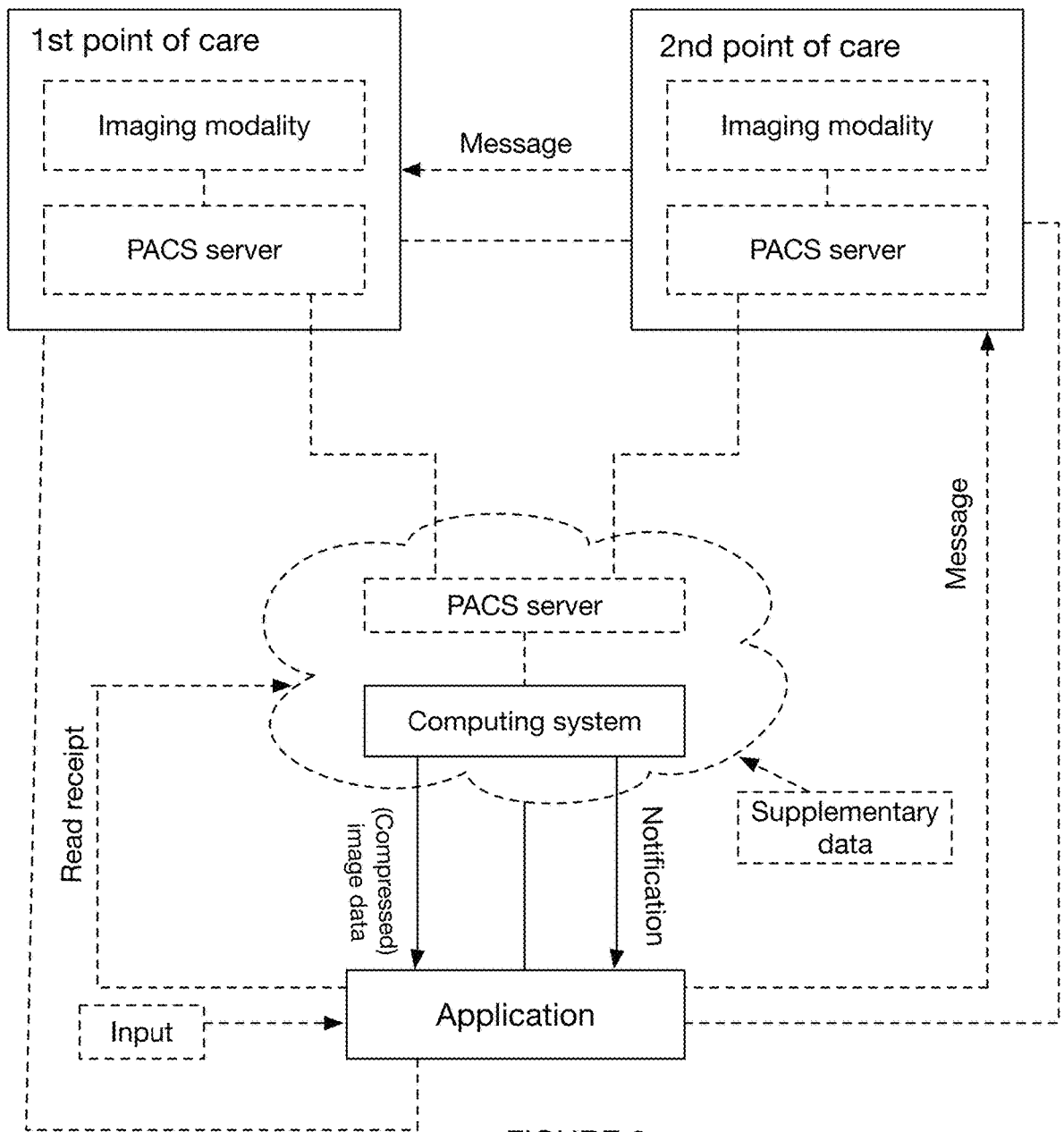
FIG. 6 depicts a variation of a method for computer-aided triage.

Transmitting information to a device associated with the $2^{nd}$ point of care (e.g., specialist, contact, etc.) S236 (e.g., as shown in FIG. 6) functions to initiate a pull from a $1^{st}$ point of care to a $2^{nd}$ point of care, which can decrease time to care, improve quality of care (e.g., better match between patient condition and specialist), or have any other suitable outcome. Preferably, the $2^{nd}$ point of care is a hub facility (e.g., specialist facility, interventional center, comprehensive stroke center, etc.). In some variations, the $1^{st}$ point of care (e.g., healthcare facility at which patient initially presents) also functions as the $2^{nd}$ point of care, such as when a suitable specialist is associated with the $1^{st}$ point of care, the $1^{st}$ point of care is a hub (e.g., specialist facility, interventional center, comprehensive stroke center, etc.), it is not advised to transfer the patient (e.g., condition has high severity based on a calculated severity score), or for any other reason.

S236 is preferably performed after (e.g., in response to) a $2^{nd}$ point of care is determined, but can additionally or alternatively be performed after a data packet (e.g., compressed data packet, encrypted data packet, etc.) has been determined, multiple times throughout the method (e.g., to multiple recipients, with multiple data packets, with updated information, after a predetermined amount of time has passed since a notification has been sent to a first choice specialist, etc.), or at any other time during the method 200.

In a first set of variations, the recipient includes a specialist, preferably a neurovascular and/or a neurosurgical specialist, and the transmitted information includes a notification sent to a mobile user device of the specialist, the notification indicating that a suspected aneurysm has been identified and recommending review of the patient's images (e.g., at a mobile application executing on the mobile user device, at a workstation of the specialist, at the mobile application and then the workstation, etc.). In specific examples, a compressed version of the images are viewable at the mobile application, wherein the specialist is recommended to view non-compressed images on a diagnostic viewer (equivalently referred to herein as a workstation) to evaluate the patient (e.g., discuss with a treating physician, make care-related decisions and/or requests, etc.). In additional or alternative specific examples, non-compressed images can be viewed at the mobile device, compressed images can be viewed at the diagnostic viewer, and/or images of any type can be viewed at any suitable devices or combination of devices.

In a second set of variations, S234 includes preparing a notification to be sent to a clinical trial research coordinator, such as a principal investigator, wherein the notification indicates that the patient is a potential candidate for a clinical trial (e.g., based on the detection of a suspected condition, based on a set of clinical trial inclusion criteria, etc.). In specific examples, a notification can be sent (e.g., automatically, triggered by the principal investigator, etc.) to a members of a clinical trial committee (e.g., physician committee), wherein approval is granted by the committee members (e.g., a majority, all, at least one, a predetermined number or percentage, etc.), such as through the client application.

4.8 Method—Receiving an Input from the Recipient and Triggering an Action Based on the Input S238

S230 can optionally additionally or alternatively include receiving an input from the recipient and triggering an action based on the input S238, which functions to determine a next step for the patient, and can include any or all of: a confirmation of the suspected condition; a rejection of the suspected condition (e.g., false positive); an acceptance by a specialist and/or care team (e.g., stroke team) to treat the patient (e.g., at a $1^{st}$ point of care, at a $2^{nd}$ point of care, etc.); a rejection of a specialist and/or care team to treat the patient; a read receipt and/or an indication of a lack or a read receipt within a predetermined time threshold; an approval to enroll the patient in a clinical trial; additional clinical information entered by a physician and/or other user; and/or any other suitable input.

In some variations, a notification is sent in S236 which prompts the individual to provide an input, wherein the input can indicate that the individual will view, has viewed, or is in the process of viewing the information (e.g., image data), sees the presence of a condition (e.g., true positive, serious condition, time-sensitive condition, etc.), does not see the presence of a condition (e.g., false positive, serious condition, time-sensitive condition, etc.), has accepted treatment of the patient (e.g., swipes right, swipes up, clicks a check mark, etc.), has denied treatment of the patient (e.g., swipes left, swipes down, clicks an 'x', etc.), wants to communicate with another individual (e.g., healthcare worker at $1^{st}$ point of care), such as through a messaging platform (e.g., native to the device, enabled by the client application, etc.), or any other input. In some variations, one or more additional notifications are provided to the individual (e.g., based on the contents of the input), which can be determined by a lookup table, operator, individual, decision engine, or other tool. In one example, for instance, if the individual indicates that the condition is a true positive, information related to the transfer of the patient (e.g., estimated time of arrival, directions to the location of the patient, etc.) can be provided (e.g., in a transfer request, wherein patient transfer to a specified location, such as the $2^{nd}$ point of care, can be initiated upon transfer request receipt). In some variants, the data (e.g., images) are displayed on the user device (e.g., mobile device, workstation) in response to user interaction with the notification (e.g., in response to input receipt). However, the input can trigger any suitable action or be otherwise used.

Additionally or alternatively, an input can automatically be received from the client application, such as a read receipt when the individual has opened the data packet, viewed the notification, or interacted with the client application in any other suitable way. In one example, if a read receipt is not received (e.g., at the remote computing system) from the device within a predetermined amount of time (e.g., 10 seconds), a second notification and/or data packet (e.g., compressed set of images) are sent to a second individual (e.g., second choice specialist based on a lookup table).

In some variations, various outputs can be sent from the client application (e.g., at the user device) to one or more recipients (e.g., to a second user device, client application on a work station, on a computing system, etc.), such as recipients associated with a first point of care (e.g., radiologists, emergency physicians, etc.). The outputs can be determined based on the inputs received at the client application associated with the individual (e.g., acceptance of case, verification of true positive, etc.), based on a lookup table, or otherwise determined. The outputs preferably do not alter the standard radiology workflow (e.g., are not shared with radiologists; radiologists are not notified), which functions to ensure that the method 200 is a true parallel process, and that the standard radiology workflow results in an independent assessment of the patient, but can additionally or alternatively cut short a workflow, bring a specialist in on the patient case earlier than normal, or affect any other process in a healthcare facility.

The outputs can include any or all of: the suspected condition, parameters (e.g., volume of an ICH) and/or scores (e.g., severity score, urgency score, etc.) associated with the suspected condition; the selection of one or more recipients of a notification (e.g., established and/or proposed care team of the patient); a proposed and/or confirmed intervention for the patient (e.g., type of procedure); an updated status (e.g., location, health status, intervention status, etc.) of one or more patients (e.g., a centralized list of all patients being reviewed by and/or treated by a specialist; a consent of the patient (e.g., for a clinical trial); an estimated parameter of the patient (e.g., estimated time of arrival at a second point of care); and/or any other suitable outputs.

The method can additionally or alternatively include initiating treatment (e.g., transfer) of the patient, wherein the treatment can include any or all of the treatment options described above, such as ay or all of: a point of care (e.g., remain at $1^{st}$ point of care, be transferred to a $2^{nd}$ point of care, etc.) at which the patient will be treated; a procedure to treat the suspected condition; a specialist and/or care team to be assigned to the patient; a clinical trial in which to enroll the patient; and/or any other suitable treatments.

In variations involving recommending the patient for a clinical trial, initiating treatment of the patient can include receiving a recommendation that the patient be considered for a clinical and/or research trial, based on one or more of: a suspected clinical condition of the patient (e.g., ICH), patient information (e.g., demographic information), a patient's willingness or potential willingness to participate, and/or any other suitable information. Initiating the recommendation can include transmitting any or all of the notifications described above (e.g., text message, call, email, etc.) to a specialist involved in the clinical and/or research trial, a specialist who has actively turned on notifications for clinical trial recruitment, a researcher, a research principal investigator, an administrative assistant, the patient himself, or any other suitable entity or individual.

Figure 7:
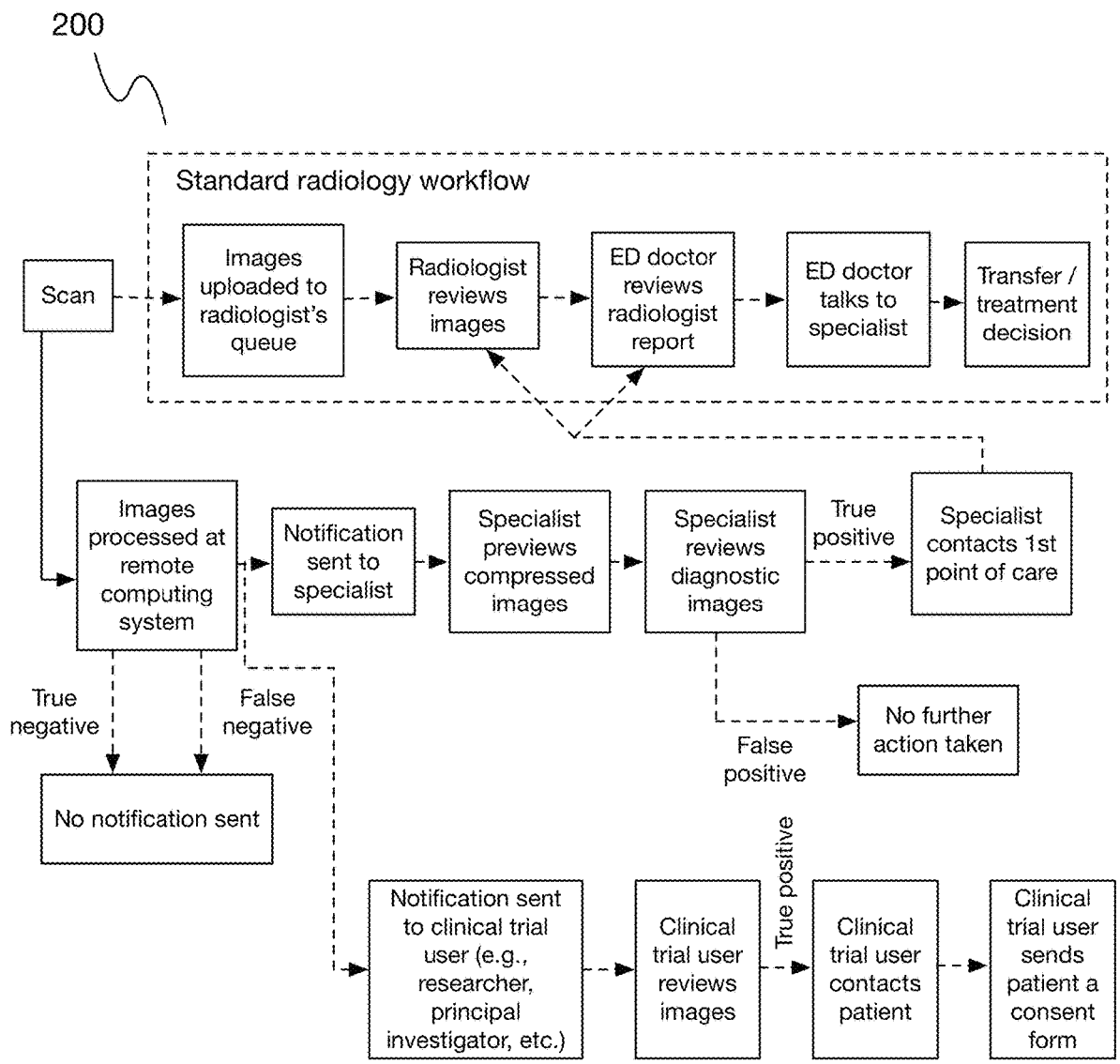
FIG. 7 depicts a variation of the method involving recommending the patient for a clinical trial.
Figure 8:
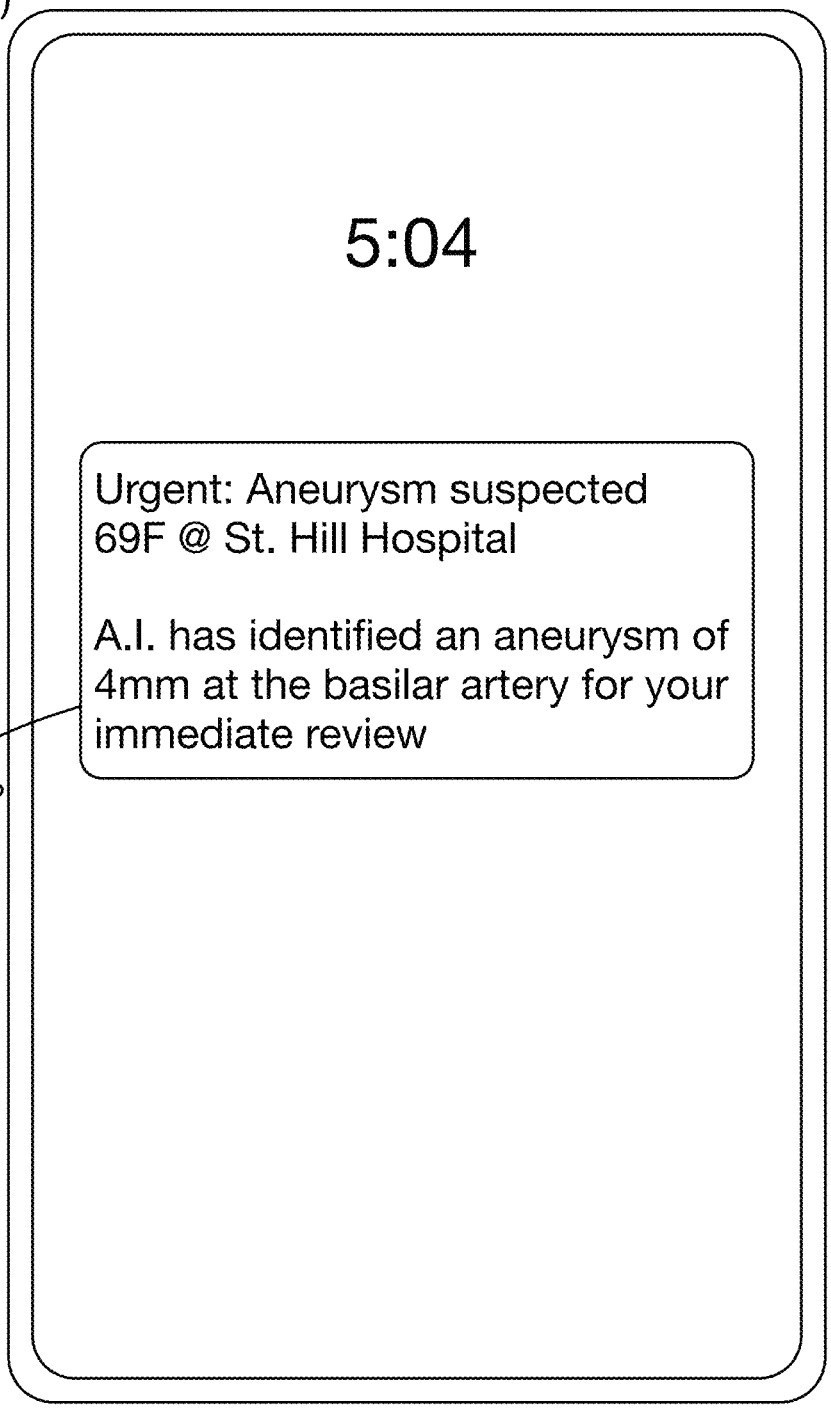
FIG. 8 depicts a variation of a notification transmitted to a device of a participant.
Figure 9:
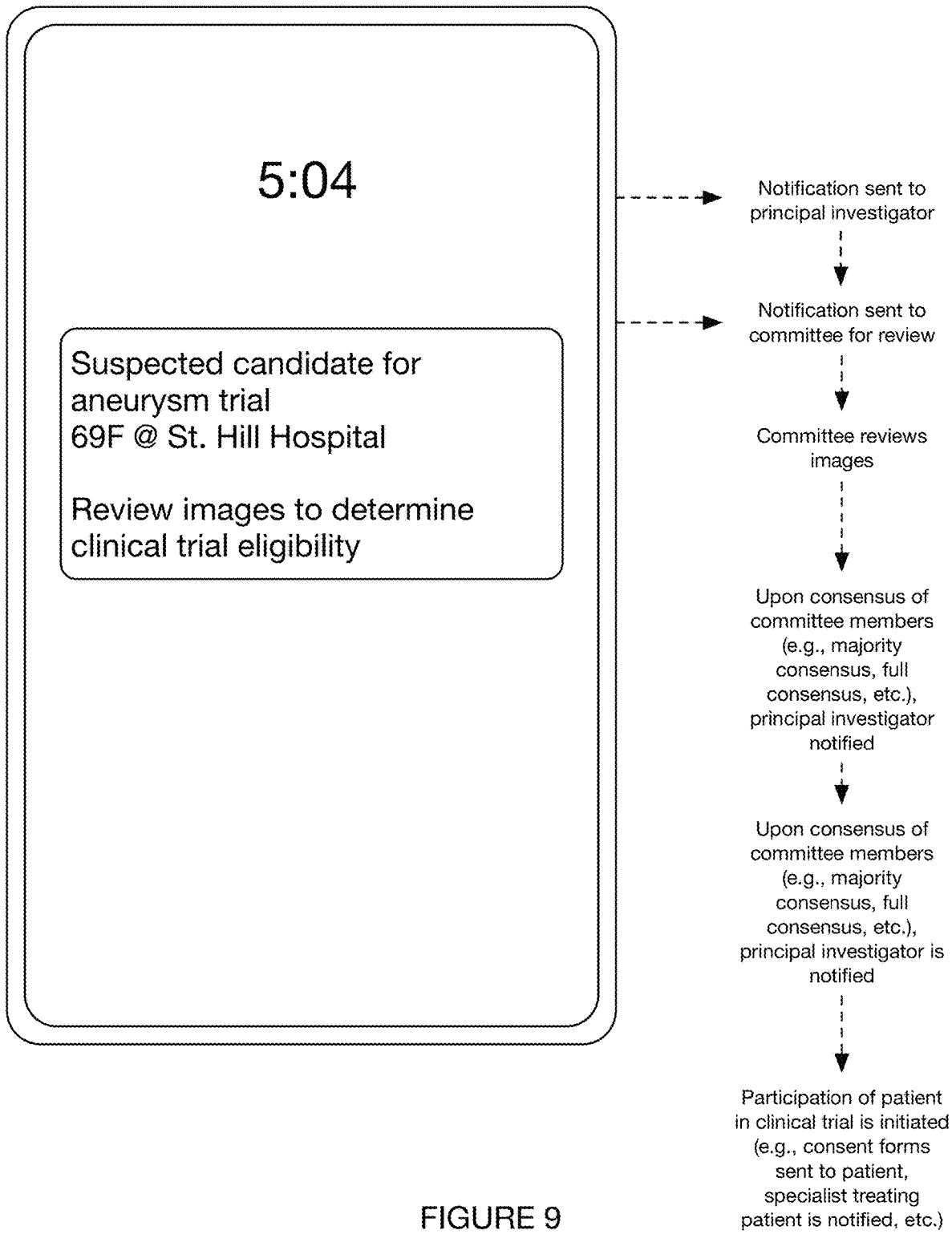
FIG. 9 depicts a variation of a notification and subsequent workflow of recommending a patient for a clinical trial.
Figure 10:
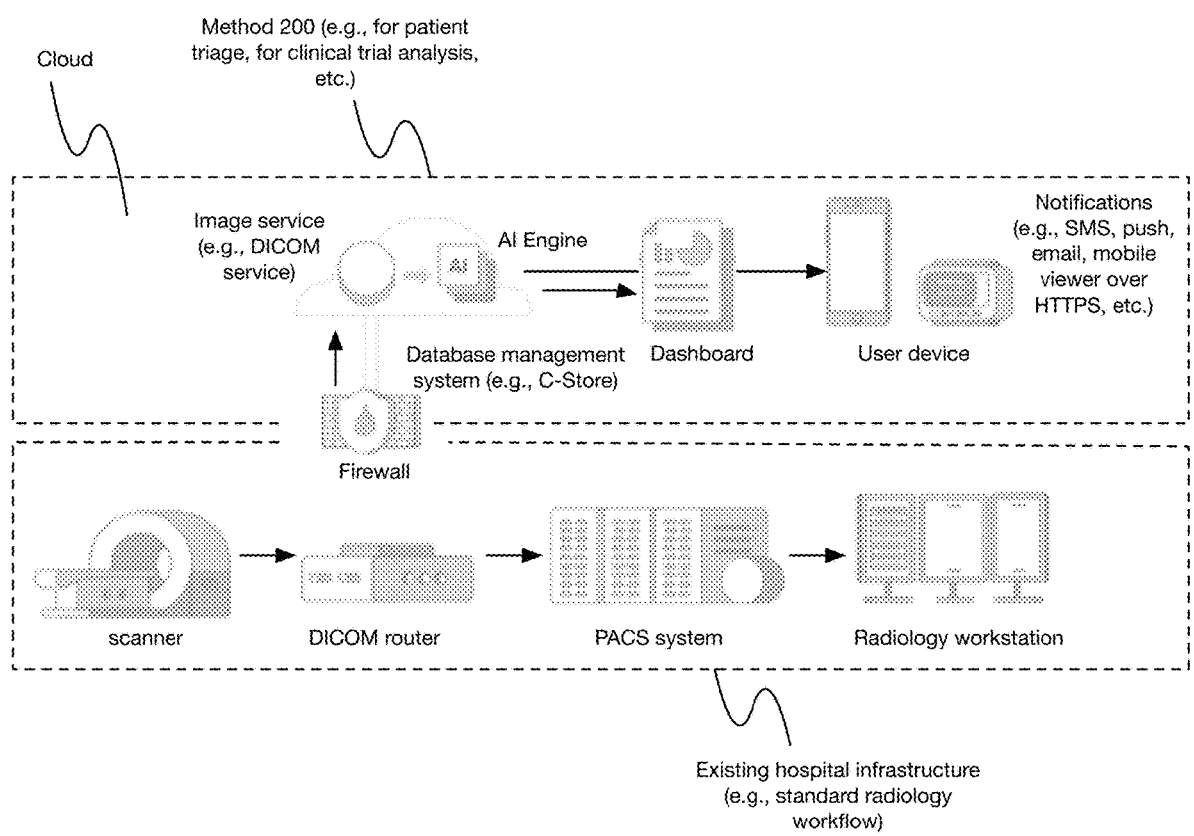
FIG. 10 depicts a variation of the system.

In specific examples (e.g., as shown in FIG. 7, as shown in FIG. 9, as performed in accordance with a system shown in FIG. 10, etc.), additional or alternative to those described above, the method functions to evaluate if a patient presenting with a potential pathology (e.g., aneurysm, stroke, ICH, LVO, etc.) qualifies for a clinical trial and if so, to alert (e.g., automatically, in a time period shorter than a determination made by a radiologist in a standard radiology workflow, etc.) a research coordinator (e.g., principal investigator) associated with the clinical trial (e.g., as shown in FIG. 8).

Figure 11:
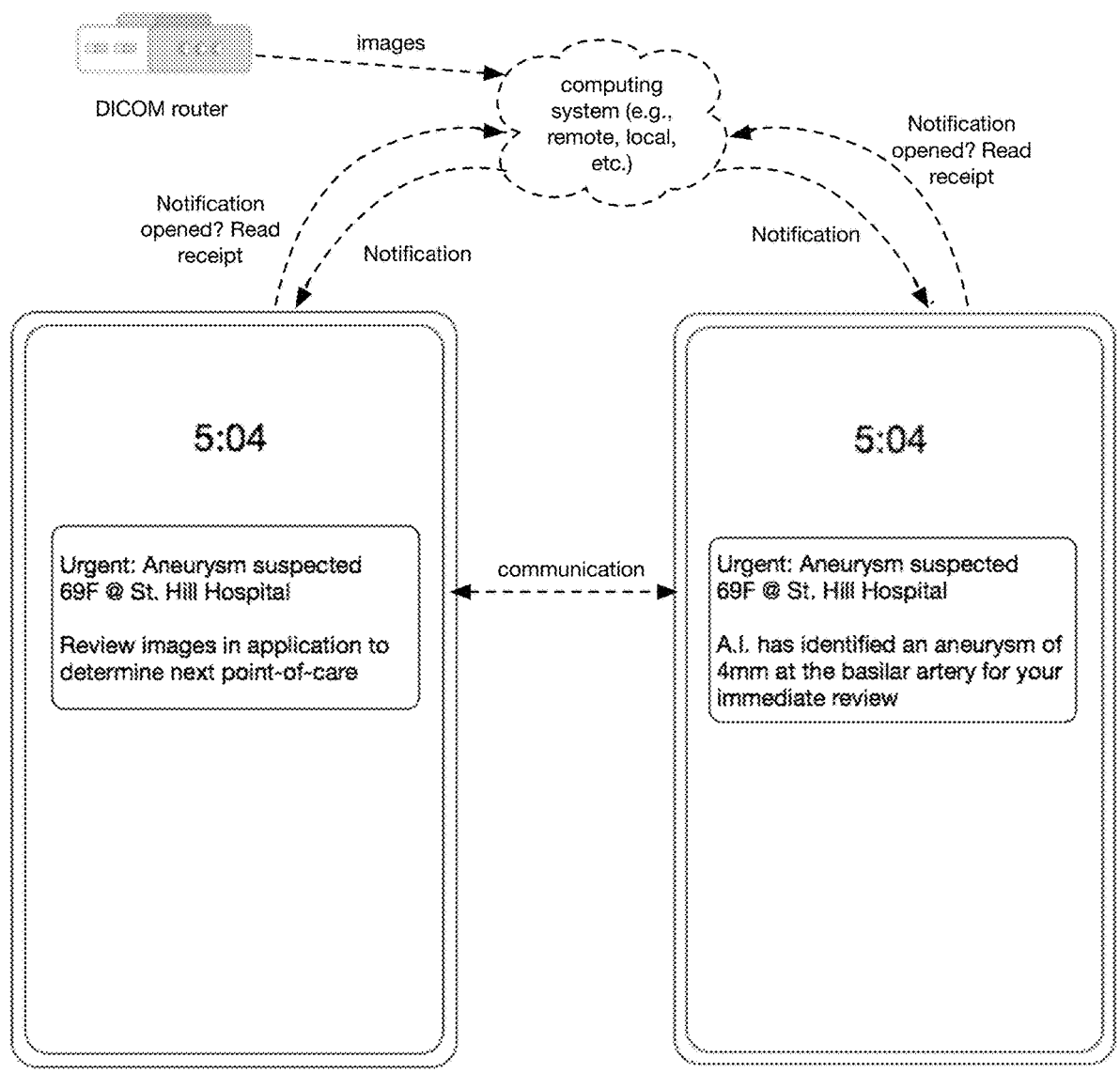
FIG. 11 depicts variations of a client application executing on a first and second user device.

The method can additionally or alternatively include establishing communication between users (e.g., texting, call, HIPAA-compliant texting, HIPAA-compliant calling, video call, etc.), such as between any or all of: multiple healthcare workers (e.g., physicians, surgeons, surgical technicians responsible for prepping for a surgical procedure, etc.), multiple research coordinators (e.g., from the same clinical trial, from different clinical trials, etc.), a healthcare worker and a research coordinator (e.g., for the research coordinator to ask questions from the surgeon, as shown in FIG. 11, etc.), a research coordinator and a patient (e.g., to submit a consent form to the patient, to receive a consent form from the patient, etc.), a healthcare worker and a patient, and/or between any other suitable users and individuals.

Additionally or alternatively, the action can include any or all of: automatically selecting and/or recommending an optimal surgical procedure for the patient (e.g., based on the location of a suspected aneurysm, based on a size of a suspected aneurysm, etc.); automatically selecting and/or recommending an optimal medical device (e.g., catheter length, aneurysm coil, etc.) for a surgical procedure; automatically assembling a surgical team for surgery of the patient (e.g., by automatically establishing a communication thread between members of the surgical care team); and/or any other processes.

4.9 Method—Aggregating Data S238

The method 200 can optionally include any number of sub-steps involving the aggregation of data involved in and/or generated during the method 200, which can function to improve future iterations of the method 200 (e.g., better match patients with a specialist, decrease time to treat a patient, increase sensitivity, increase specificity, etc.). The aggregated data is preferably used in one or more analytics steps (e.g., to refine a treatment option, make a recommendation for a drug or procedure, etc.), but can additionally or alternatively be used for any other suitable purpose. In some variations, for instance, aggregated data is used to train and/or re-train one or more trained models (e.g., machine learning models, deep learning models, neural networks, etc.) used in the method 200.

In a first set of variations, the outcomes of the patients examined during the method 200 are recorded and correlated with their corresponding data packets, which can be used to assess the success of the particular treatment options chosen and better inform treatment options in future cases.

In specific examples, these outcomes along with the set of inputs used to determine these outcomes are analyzed and used to retrain any or all of the trained models used to reach a set of outcomes.

4.10 Variations

In a first set of variations, detecting an aneurysm in the method 200 includes filtering a set of images based on associated metadata; preprocessing the set of images; registering the set of images, and segmenting the set of images.

In specific examples, the method 200 includes: receiving a set of images corresponding to a CTA head scan of a patient; verifying that the set of images is applicable to the method 22 by inspecting DICOM metadata tags and determining that the set of images satisfies all of a predetermined set of metadata inclusion criteria; checking for a set of exclusion criteria (e.g., metallic artifact), wherein upon determining that a predetermined number (e.g., 1, 2, 10, between 10 and 100, greater than 100, etc.) of voxels of the set of images has an HU value above a predetermined threshold (e.g., 3000 HU), the set of images is eliminated from further processing; cropping the set of images to keep only a relevant region or regions (e.g., brain region, head region, etc.) of the patient; applying a clipping transformation to the set of images to remove irrelevant HU values below a predetermined threshold (e.g., between −500 and −520, less then −500, etc.) and above a predetermined threshold (e.g., greater than 1000, between 1000 and 1100, etc.); normalizing the HU values of the set of images based on the mean HU value and the standard deviation (e.g., subtracting the mean HU value and dividing by the standard deviation); optionally resampling the set of images to a predetermined resolution (e.g., 1 mm) in all dimensions; optionally cropping the set of images to include a Circle of Willis region through a z-axis cropping (e.g., from the top of the scan) and an x-y plane cropping (e.g., from the center of the scan); comparing the set of images (e.g., the Circle of Willis region) with an atlas in a registration process including a deep learning model (e.g., deep CNN), wherein the registration produces a transformation to apply to the images (e.g., the original images); optionally cropping and/or resampling the images; segmenting the images with a deep learning model (e.g., a U-net) to determine the presence of a suspected aneurysm and its location; calculating a probability score associated with each voxel corresponding to the suspected aneurysm; summing the probability scores and comparing with the threshold; in an event that the scores are above the threshold, determining an action, which can optionally include any or all of: determining a recipient (e.g., specialist, research coordinator, etc.); transmitting information to a device associated with the recipient; receiving an input associated with and/or from the recipient (e.g., read receipt, input, etc.) and optionally triggering an action based on the input (e.g., initiating transfer, identifying a clinical trial, etc.). Additionally or alternatively, any or all of the action (e.g., recommending a procedure, recommending a surgical device, etc.) can be performed in absence of determining a recipient.

In a second set of variations (e.g., as shown in FIG. 12), additional or alternative to the first, the method 200 includes receiving a set of images (e.g., CTA images) from an imaging modality; optionally filtering the set of images based on one or more pieces of metadata associated with the images; optionally filtering the set of images based on one or more image-based filtering processes (e.g., based on HU values) optionally pre-processing the set of images (e.g., cropping the set of images, resampling the set of images, etc.); performing a registration process for the set of images (e.g., the preprocessed set of images) with a set of one or more neural networks to determine a transformation (e.g., affine transformation) for the set of images; applying the transformation to the set of images; performing a set of one or more segmentation processes to detect a suspected set of aneurysms and any features (e.g., size, location, etc.) associated with the set of aneurysms; determining a set of scores based on and/or with the segmentation processes; optionally aggregating multiple sets of scores (e.g., from multiple segmentation processes, from multiple suspected aneurysms, from multiple regions of the set of images processed independently, etc.); optionally comparing the set(s) of scores with one or more thresholds to determine and/or confirm a suspected aneurysm and/or aneurysm features; and triggering an action based on the suspected aneurysm and/or features.

In a first set of specific examples, the set of segmentation processes includes a fixed location segmentation process (e.g., as described above).

In a second set of specific examples, the set of segmentation processes includes a dynamic location segmentation process (e.g., as described above).

In a third set of specific examples, the set of segmentation processes includes a dynamic location segmentation process (e.g., as described above) and a fixed location segmentation process (e.g., as described above), wherein output scores from these segmentation processes can be aggregated and used in determining the set of suspected aneurysms. Additionally or alternatively, the scores can be non-aggregated and used independently to assess for suspected aneurysms.

Additionally or alternatively, the method can include any other suitable processes.

Although omitted for conciseness, the preferred embodiments include every combination and permutation of the various system components and the various method processes, wherein the method processes can be performed in any suitable order, sequentially or concurrently.

As a person skilled in the art will recognize from the previous detailed description and from the figures and claims, modifications and changes can be made to the preferred embodiments of the invention without departing from the scope of this invention defined in the following claims.

We claim:

1. A method for computer-aided triage of a suspected aneurysm, the method comprising:
receiving a set of images associated with a patient and taken at an imaging modality at a point of care;
registering the set of images with a set of reference images, wherein registering the set of images comprises:
processing the set of images with a first neural network to determine a set of locations in the set of images;
comparing the set of locations with a second set of locations of the set of reference images;
determining a transformation based on the comparison; and
transforming the set of images based on the transformation;
segmenting a predicted aneurysm from the set of images with a second neural network, wherein segmenting the predicted aneurysm from the set of images comprises determining a set of probability scores associated with a set of voxels of the segmented predicted aneurysm;
aggregating the set of probability scores to determine an aggregated score;
comparing the aggregated score with a predetermined threshold;
in an event that the aggregated score exceeds the predetermined threshold, automatically detecting the suspected aneurysm, wherein the suspected aneurysm is the predicted aneurysm;
in response to automatically detecting the suspected aneurysm, triggering an action at a client application executing on a mobile user device associated with a specialist, wherein the specialist is associated with a second point of care separate and distinct from the first point of care, wherein the action comprises the transmission of the set of images to the client application for review by the specialist; and
monitoring for an input from the specialist at the client application, wherein in response to receiving the input, the method further comprises automatically initiating a transfer of the patient from the first point of care to the second point of care, wherein in an event that the input is not received within a predetermined period of time, triggering a second action at a second mobile user device associated with a second specialist.

2. The method of claim 1, wherein the segmentation process comprises multiple segmentation subprocesses.

3. The method of claim 2, wherein the multiple segmentation subprocesses are performed in parallel.

4. The method of claim 2, wherein the multiple segmentation subprocesses comprises a first subprocess, wherein the first subprocess is a single stage segmentation process performed based on a predetermined set of regions.

5. The method of claim 4, wherein the predetermined set of regions is associated with a highest likelihood of aneurysm occurrence.

6. The method of claim 4, wherein the multiple segmentation subprocesses comprises a second subprocess, wherein the second subprocess is a multi-stage segmentation process comprising a set of multiple stages, wherein the set of multiple stages is configured to iteratively refine the predicted aneurysm.

7. The method of claim 1, wherein the set of images transmitted to the client application comprises a compressed version of the set of images taken at the imaging modality.

8. The method of claim 7, further comprising displaying a high-resolution version of the set of images on a second device associated with the specialist.

9. The method of claim 8, wherein the second device is a workstation at the second point of care.

10. The method of claim 1, wherein the automatically detecting the suspected aneurysm supplements a standard radiology workflow.

11. A method for computer-aided triage of a suspected aneurysm, the method comprising:
receiving a set of images associated with a patient and taken at an imaging modality at a point of care;
automatically registering the set of images with a set of reference images based on a first set of one or more neural networks;
automatically identifying a predicted aneurysm in the set of images with a set of segmentation processes, wherein the set of segmentation processes comprises:
a first segmentation process performed with a second set of one or more neural networks, wherein the first segmentation process produces a first set of probability scores;
a second segmentation process performed with a third set of one or more neural networks, wherein the second segmentation process produces a second set of probability scores;
aggregating the first and second sets of probability scores to determine an aggregated set of scores;
comparing the aggregated set of scores with a predetermined set of thresholds;
determining the suspected aneurysm based on the comparison, wherein the suspected aneurysm is the predicted aneurysm; and
in response to determining the suspected aneurysm, triggering an action at a client application executing on a mobile user device associated with a specialist; and
monitoring for an input from the specialist at the client application, wherein in an event that the input is not received within a predetermined period of time, triggering a second action at a second mobile user device associated with a second specialist.

12. The method of claim 11, wherein each of the second set of one or more neural networks and the third set of one or more neural networks comprises a feed-forward deep convolutional neural network.

13. The method of claim 11, wherein the first segmentation process comprises a single stage segmentation process.

14. The method of claim 13, wherein the single stage segmentation process is performed based on a predetermined set of regions in the set of images, wherein the predetermined set of regions is associated with a highest likelihood of aneurysm occurrence.

15. The method of claim 13, wherein the second segmentation process comprises a multi-stage segmentation process.

16. The method of claim 11, wherein the third set of neural networks comprises multiple neural networks applied in a set of multiple stages, wherein the set of multiple stages is configured to iteratively refine the predicted aneurysm.

* * * * *